US009545339B2

(12) United States Patent
Serdarevic et al.

(10) Patent No.: US 9,545,339 B2
(45) Date of Patent: Jan. 17, 2017

(54) CORNEAL VITRIFICATION, METHODS AND DEVICES TO PRODUCE CORNEAL VITRIFICATION AND METHODS OF USE THEREOF

(71) Applicants: Olivia Serdarevic, Goshen, NY (US); Michael Berry, Austin, TX (US); Donald F. Heller, Somerset, NJ (US)

(72) Inventors: Olivia Serdarevic, Goshen, NY (US); Michael Berry, Austin, TX (US); Donald F. Heller, Somerset, NJ (US)

(*) Notice: Subject to any disclaimer, the term of this patent is extended or adjusted under 35 U.S.C. 154(b) by 0 days.

(21) Appl. No.: 14/512,952

(22) Filed: Oct. 13, 2014

(65) Prior Publication Data

US 2015/0133901 A1 May 14, 2015

Related U.S. Application Data

(60) Provisional application No. 61/903,213, filed on Nov. 12, 2013.

(51) Int. Cl.
*A61F 9/008* (2006.01)
*A61F 9/007* (2006.01)
*A61N 7/00* (2006.01)

(52) U.S. Cl.
CPC .............. *A61F 9/008* (2013.01); *A61F 9/0079* (2013.01); *A61F 2009/00872* (2013.01); *A61N 7/00* (2013.01)

(58) Field of Classification Search
CPC .................. A61F 9/008; A61F 9/0081; A61F 2009/00872; A61F 2/14; A61F 2/142; A61F 2/147

(Continued)

(56) References Cited

U.S. PATENT DOCUMENTS

2003/0093066 A1* 5/2003 Peyman .............. A61F 9/00812
606/5
2004/0243112 A1 12/2004 Bendett et al.
(Continued)

FOREIGN PATENT DOCUMENTS

DE 10061968 A1 * 12/2000

OTHER PUBLICATIONS

International Search Report and Written Opinion from International Application No. PCT/US2014/060286 dated Jan. 26, 2015.

*Primary Examiner* — Ahmed Farah
(74) *Attorney, Agent, or Firm* — Greenberg Traurig, LLP

(57) ABSTRACT

The invention includes: a new composition of matter (a composite comprising a naturally occurring in vivo cornea in an in situ eye together with at least one volume of vitrified non-naturally occurring corneal stromal tissue formed within the naturally occurring corneal stromal tissue) wherein the vitrified tissue is modified in structure and properties from its naturally occurring condition into a non-naturally occurring glass-like condition with modifications including but not limited to increased eletastic modulus; methods for producing and using the new composition of matter for modifying cortical structure and properties, including but not limited to corneal optical aberrations; wound closure adhesion and transplant adhesion; and a photovitrification system for producing the new composition of matter comprising at least one photon source with controllable treatment parameters. A reverse template can be added to corneal vitrification systems to increase vitrification and modifications of structure and properties.

13 Claims, 19 Drawing Sheets

(58) Field of Classification Search
USPC ........ 606/4–6; 607/88, 89, 96, 100; 623/4.1, 623/5.11–5.16; 128/898
See application file for complete search history.

(56) References Cited

U.S. PATENT DOCUMENTS

| | | | |
|---|---|---|---|
| 2006/0216329 A1* | 9/2006 | Peyman | A61F 9/008 424/428 |
| 2007/0167935 A1 | 7/2007 | Serdarevic | |
| 2010/0198348 A1* | 8/2010 | Hiles | A61F 2/142 623/5.16 |
| 2010/0210996 A1* | 8/2010 | Peyman | A61F 7/007 604/20 |
| 2011/0071509 A1 | 3/2011 | Knox et al. | |
| 2012/0232648 A1* | 9/2012 | Kahook | A61F 2/16 623/5.16 |

* cited by examiner

CORNEAL VITRIFICATION, METHODS AND DEVICES TO PRODUCE CORNEAL VITRIFICATION AND METHODS OF USE THEREOF

RELATED APPLICATION

This application claims the priority of U.S. provisional application Ser. No. U.S. Ser. No. 61/903,213, entitled "LASER DEVICES FOR CORNEAL SHAPING AND METHODS OF USE THEREOF," filed Nov. 12, 2013, which is incorporated herein by reference in its entirety for all purposes.

TECHNICAL FIELD

The instant invention is related to vitrification of corneal stromal tissue of an in vivo cornea in an in situ eye. The instant invention is also related to methods and devices that produce corneal vitrification, such as methods and devices for photovitrification that utilize a photon source to produce vitrification of corneal tissue; and methods of use thereof such as for modifying corneal structure and corneal properties, including corneal optical aberrations, of in vivo and in situ human corneas.

BACKGROUND OF INVENTION

The cornea is the transparent front part of the eye that covers the iris, pupil, and anterior chamber. The cornea is the main optical element of the eye that focuses light.

BRIEF SUMMARY OF INVENTION

The instant invention provides specifications for a composition of matter that is a composite of a naturally occurring in vivo cornea in an in situ eye together with at least one volume of non-naturally occurring corneal stromal tissue formed within the naturally occurring corneal stromal tissue of an in vivo cornea of an in situ eye wherein the at least one volume of non-naturally occurring corneal stromal tissue is at least 1% vitrified thereby modifying its structure and properties from naturally occurring structure and properties to non-naturally occurring glass-like structure and properties. The instant invention also provides methods and devices for producing corneal vitrification and for using corneal vitrification.

DETAILED DESCRIPTION OF VARIOUS EMBODIMENTS

Among those benefits and improvements that have been disclosed, other objects and advantages of this invention can become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Any alterations and further modifications of the inventive feature illustrated herein, and any additional applications of the principles of the invention as illustrated herein, which can normally occur to one skilled in the relevant art and having possession of this disclosure, are to be considered within the scope of the invention.

Throughout the specification, the following terms take the meanings explicitly associated herein, unless the context clearly dictates otherwise. The phrases "In one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

The present invention involves corneal vitrification which, as used herein, is understood to be the production of a new composition of matter that is a composite comprising a naturally occurring in vivo cornea of an in situ eye together with at least one volume of non-naturally occurring corneal stromal tissue formed within the naturally occurring corneal stromal tissue of an in vivo cornea of an in situ eye wherein the at least one volume of non-naturally occurring corneal stromal tissue is at least 1% vitrified thereby modifying its structure and properties from naturally occurring structure and properties to non-naturally occurring glass-like structure and properties.

Figure 1:
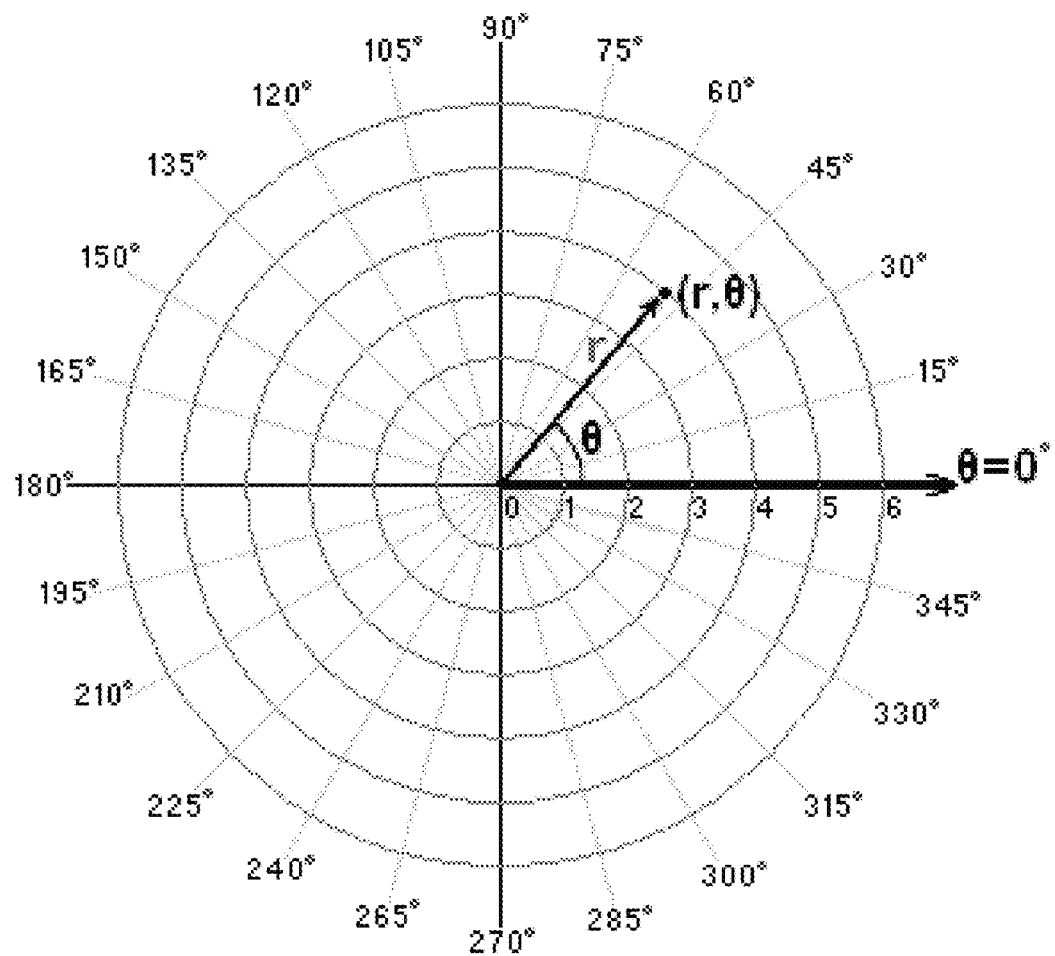
FIG. 1: Two-dimensional (2-D) polar coordinates.
Figure 2:
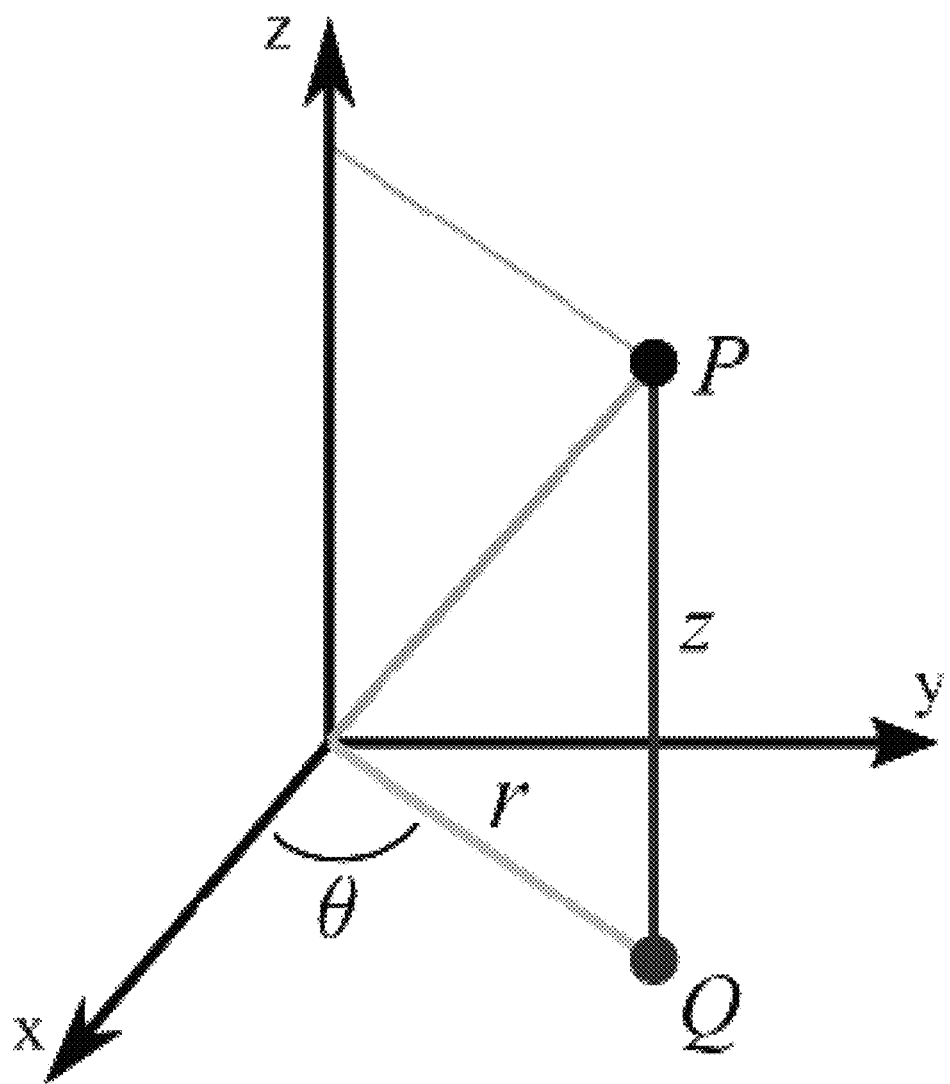
FIG. 2: Three-dimensional (3-D) cylindrical coordinates.

FIG. 1 shows the polar coordinate system that is used to describe two spatial coordinates $(r,\theta)$ on the cornea anterior surface. A given point on the cornea anterior surface can be specified in terms of the radius (r) and the angle ($\theta$) coordinates of that point with respect to a centration reference ($r=0$) and an angular reference ($\theta=0$, usually taken to be the 3 o'clock angle viewing the eye en face). There is a third spatial (axial) coordinate—the depth (z) from the cornea anterior surface. FIG. 2 shows the three-dimensional (3-D) cylindrical coordinate system that is used to specify a 3-D point P within the cornea at a depth z from the two-dimensional (2-D) surface point Q. In FIG. 2, the depth (axial coordinate) z is shown as increasing vertically upward but z is shown as increasing vertically downward in the following FIG. 3.

Figure 3:
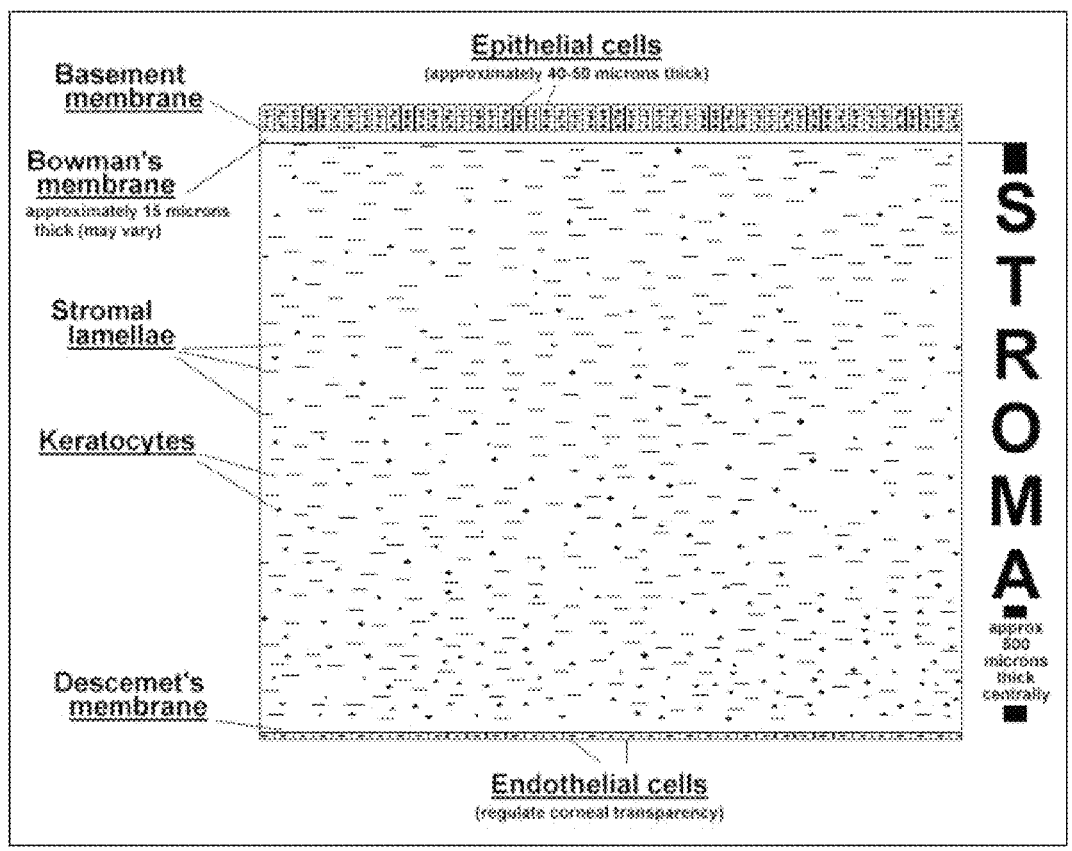
FIG. 3: Schematic cross-section of the cornea.

As described herein, human corneal nano-, micro- and macrostructure and properties are specified in their naturally-occurring, normal (i.e., non-vitrified) in vivo condition as they occur in situ. FIG. 3 shows a schematic cross-section of a human cornea with identification of structural features that are typically organized in layers at different depths z from the anterior corneal surface (top in FIG. 3). The central cornea thickness is ca. 550 μm, comprising (proceeding from the anterior to the posterior surface, e.g., from $z=0$ to $z=550$ μm): 1—the tear film—not shown in FIG. 3, ca. 3 μm thickness;

2—the epithelium—ca. 56 μm central thickness; the epithelium is anchored to the underlying cornea by a basement membrane (aka corneal anterior basement membrane); the epithelium has a range of thicknesses (typically 40 to 70 μm) at noncentral ($r>0$) $r,\theta$ locations;

3—Bowman's layer (aka Bowman's membrane or the anterior limiting lamina)—an acellular layer ca. 15 μm thickness in contact with the epithelial basement membrane; often considered to be the acellular portion of the stroma 4—the stroma—ca. 500 μm central thickness; populated by keratocytes; and 5—posterior structures—Descemet's membrane, Dua's layer—not shown, and the endothelium. For purposes of the instant invention, Bowman's layer is considered to be the acellular portion of the anterior stroma.

Figure 4:
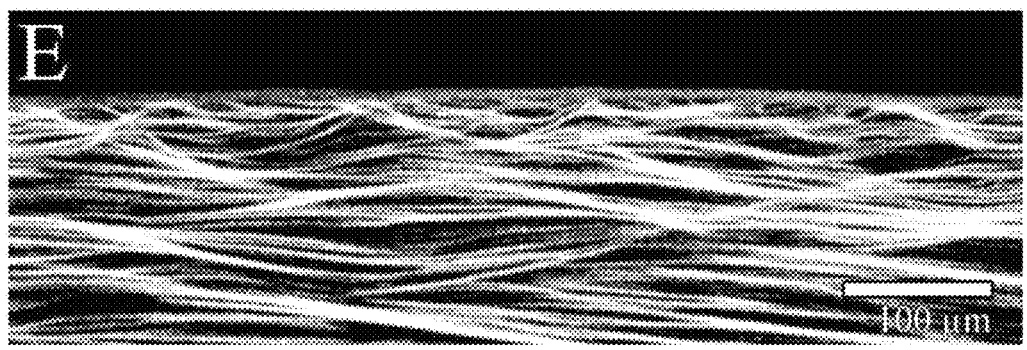
FIG. 4: Nonlinear optical microscopy image of anterior-most corneal stroma

For purposes of the instant disclosure, the corneal tissues or components thereof that are specifically intended to be materially affected by the treatment described herein are designated as "targets" while other (non-targeted) corneal tissues or components thereof are intended not to be materially affected by the treatment described herein and, consequently, are areas where deleterious effects are intended to be minimized. The corneal stromal tissue, including Bowman's layer, is the target of this invention. The stromal thickness in the central cornea is approximately 500 μm and increases to approximately 600 μm or more in the peripheral cornea. In some embodiments, the anterior region (for example, the anterior one-third or approximately the anterior 150 to 200 μm thickness) of the stroma including the Bowman's layer is the targeted region. In some embodiments, the anterior stroma excluding Bowman's layer is the targeted region. This anterior stromal region includes "sutural" collagen lamellae having anisotropic structure and its normally associated biomechanical properties. FIG. 4 shows the microstructure of Bowman's layer (top) and stroma to a depth of ca. 160 μm; the epithelium is not shown in the figure. In contrast to the posterior stroma that consists of collagen fibrils and lamellae forming regular layers aligned parallel to the anterior corneal surface with low interlamellar adhesion, the most anterior stroma consists, in part, of randomly aligned fibrils and lamellae that are highly interconnected with branching across multiple layers providing much greater interlamellar adhesion and modulus. Many anterior fibrils are transverse (also known as oblique) and even form "sutures" into Bowman's layer. In some embodiments, this anterior stromal tissue is targeted to maximize beneficial treatment effects and to minimize deleterious effects to all corneal structures.

The stroma is the main structural portion of the cornea, defining the shape of the cornea. In naturally occurring in vivo conditions, the stroma is a fiber/matrix composite with unique optical properties. The stroma has high transparency with little or no light scattering. The stroma also has unique anisotropic biomechanical properties that are a function of both temperature and the time during which the stroma experiences a particular temperature, as described in detail below. Keratocytes are the main cells within the stroma, accounting for as much as 10% of the dry mass of the stroma. The main fiber constituent in the stromal fiber/matrix composite is Type I collagen. Type I collagen is highly organized in fibrils and lamellae in in vivo corneal stroma at normal physiological temperature. The constituents in the stromal fiber/matrix composite, apart from cells, are termed the extracellular matrix (ECM); the ECM comprises, in addition to the collagen fiber nanostructural constituents, proteoglycans (PGs), glycosaminoglycans (GAGs), water, inorganic ions, and other nanostructural constituents. Water comprises over 75% by weight of in vivo corneal stroma in its naturally occurring condition.

In its naturally occurring condition, the in vivo cornea of the in situ eye has a lens-like structure that focuses light rays entering the eye. Additional focusing is provided by the crystalline lens of the eye in order to form an image on the retina, the photoactive portion of the eye. The retina has structures (the macula and the fovea within the macula) that are important for central vision. In many cases, images are not correctly focused on the retina due to optical aberrations in the cornea and/or the crystalline lens. In some cases, another cause of incorrect focusing is an incorrect axial length of the eye that does not match the focusing power of the cornea plus lens. In some embodiments, modification of corneal optical aberrations by the instant invention can be used to form correctly focused images on the retina. In some cases, ocular pathologies that cause central visual field deficits and scotomata, including but not limited to retinal disorders such as age-related macular degeneration, degrade vision because images are focused onto dysfunctional portions of the macula. In some embodiments, modification of corneal optical aberrations by the instant invention can be used to magnify and/or relocate images in order to use functional portions of the retina.

In some cases, the in vivo cornea of the in situ eye has naturally occurring and/or iatrogenic ectatic disorders, such as keratoconus or ectasia after corneal ablative surgery, that can be progressive in nature. In some embodiments, increase of corneal elastic modulus by the instant invention can be used to reduce the progression of these disorders. In some embodiments, modification of corneal optical aberrations by the instant invention can also be used to improve vision in these cases with ectasia.

The term "corneal vitrification" used in connection with the invention described herein is understood to mean the type of vitrification produced in an in vivo cornea of an in situ eye involving the production of a new composition of matter that is a composite comprising a naturally occurring in vivo cornea of an in situ eye together with at least one volume of non-naturally occurring corneal stromal tissue formed within the naturally occurring corneal stromal tissue of an in vivo cornea of an in situ eye wherein the at least one volume of non-naturally occurring corneal stromal tissue is at least 1% vitrified thereby modifying its structure and properties from naturally occurring structure and properties to non-naturally occurring glass-like structure and properties. The term "corneal photovitrification" (PV) used in connection with the invention described herein is understood to mean corneal vitrification produced in an in vivo cornea of an in situ eye by photons. As an example, the mechanical properties of the vitrified stromal tissue can be modified compared to those of the naturally occurring stromal tissue. As an example, the elastic modulus of the vitrified stromal tissue can be increased compared to the elastic modulus of the naturally occurring unvitrified cornea. As an example, the increase in elastic modulus of the vitrified stromal tissue can comprise at least one of: a 10% increase of an axial modulus (wherein the axial modulus is through the cornea from anterior stroma to posterior stroma), at least a 10% increase of a shear modulus, or any combination thereof. The instant invention comprises at least three types of corneal photovitrification or any combination thereof that can be distinguished:

photochemical (in which photochemical reactions cause vitrification), photomechanical (in which photons produce mechanical effects that cause vitrification), and photophysical (in which photons produce physical effects, including heating, that cause vitrification).

In some embodiments, two or more types of PV may occur, such as the combination of photochemical and photophysical procedures. In some embodiments, photophysical PV can include the use of photon absorption modifiers including dyes, nanorods, or any combination thereof. In some embodiments, it is understood that the term "light" also encompasses any form of electromagnetic energy (i.e., photons) including, but not limited to, photons with wavelengths that span the ultraviolet (UV), visible (VIS), near infrared (NIR), infrared (IR), microwave (MW) and radiofrequency (RF) regions of the electromagnetic spectrum with a range of wavelengths from approximately 300 nanometers to 1 meter. In some embodiments, photons can be used at sufficient intensity to cause multiphoton (for example, simultaneous two-photon) absorption that modifies in vivo corneal stromal tissue of an in vivo cornea of an in situ human eye to produce corneal stromal modification, including vitrification with increased targeting of beneficial modifications.

In some embodiments, modification of corneal tissue is provided by using non-light energy sources including, but not limited to, acoustic energy sources that produce ultrasound at frequencies in the range of approximately 20 kilohertz to 200 megahertz; in this case, acoustic energy produces acoustic vitrification.

In some embodiments, methods of corneal vitrification include the application of external stress to the anterior surface of the cornea during corneal vitrification treatment to enhance modifications of structure and properties in the vitrified volume/s of stromal tissue. The addition of external stress applied to the anterior surface of the cornea is associated with a pressure applied to at least one treated volume of the in vivo corneal stromal tissue of an in vivo cornea of an in situ eye to enhance modifications of structure and properties of the vitrified stromal tissue. As an example, the external pressure densifies in vivo corneal stroma of an in vivo cornea of in situ eye, wherein the external stress is associated with an enhancement of at least 5% in density of the corneal stroma (for example, an increase in number of fibrils per unit volume) within the at least one treated volume of the in vivo corneal vitrified stromal tissue of an in vivo cornea of an in situ eye.

In some embodiments, heating corneal stromal tissue produces modifications to the structure and properties of the tissue including, but not limited to: vitrification, elastic modulus, or any combination thereof. As used herein, at least one photovitrification (PV) heat affected zone ("HAZ") is a tissue volume affected by PV treatment (Tx) within a PV Tx area; the PV Tx area is defined to be the anteriormost surface of the PV HAZ and the PV HAZ extends into the tissue axially to a maximum depth $z_{max}$. The PV HAZ geometric volume is typically defined in 3-D cylindrical coordinates r,θ,z—see FIG. 2.

In some embodiments, the corneal vitrification in the PV HAZ is produced, at least in part, by "moderate temperature fast heating"—see below.

Corneal stromal tissue vitrification in accordance with the present inventive system(s) can involve modifications to in vivo corneal stromal tissue including, but not limited to:
A—modifications of stromal nano-, micro- and macrostructure, including but not limited to the fiber/matrix composite;
B—modifications of stromal fiber/matrix and cellular functions, including, but not limited to, metabolism, motility and interactions including signaling on all scales;
C—modifications of stromal tissue properties, including, but not limited to, mechanical, optical, thermal and transport properties, on all scales;
D—or any combination thereof.
For example, in some embodiments, in accordance with the instant inventive system(s), the following modification to in vivo corneal stromal tissue occurs for moderate temperature (for example, up to a maximum temperature $T_{max}$ of ca. 100° C.), fast heating (for example, with a thermal history comprising less than ca. 1 second of heating to $T_{max}$ and of remaining at $T_{max}$ prior to cooling):
increased elastic modulus of in vivo corneal stromal tissue within the treated volume;
wherein the treated volume comprises corneal stromal tissue treated in the temperature range between the maximum temperature $T_{max}$ to a lower temperature $T_{max}$-5° C.; wherein the increase in elastic modulus of the vitrified stromal tissue can comprise at least one of: a 10% increase of an axial modulus (wherein the axial modulus is through the cornea from anterior stroma to posterior stroma), at least a 10% increase of a shear modulus, or any combination thereof.

In some embodiments, corneal stromal modification includes vitrification of at least 1% of at least one treated volume element within at least one HAZ; said treated volume having been treated in the temperature range between the maximum temperature $T_{max}$ to a lower temperature $T_{max}$-5° C.

In some embodiments, beneficial modifications including, but not limited to those described above, are maximized (with respect to considerations including, but not limited to, targeting, safety, effectiveness and predictability) and, in addition, deleterious effects including, but not limited to, deleterious alterations to the structure, function and properties of both the non-vitrified and vitrified stromal volumes are minimized.

In some embodiments, the range of maximum temperature $T_{max}$ used to modify tissue within the heat affected zone (HAZ) includes, but is not limited to, $T_{max}$ between 50° C. to 100° for a range of thermal history between 20 milliseconds (ms) to 2000 ms. In some embodiments, the ranges of modifications of treated in vivo corneal stromal tissue within the HAZ include, but are not limited to, vitrification between 1 and 50% in the treated volume and corneal elastic modulus increase between 10% to 1000% with at least one of: an increase between 10% and 1000% of an axial modulus (wherein the axial modulus is through the cornea from anterior stroma to posterior stroma), at least an increase between 10% and 1000% of a shear modulus, and any combination thereof, wherein the treated volume comprises tissue treated in the temperature range between the maximum temperature $T_{max}$ to a lower temperature $T_{max}$-5° C.

Reaction rates for rate processes have temperature-dependent rate coefficients $k_i(T)$ with typical Arrhenius equation behavior for each rate process i:

$$k_i(T)=A_i \exp(-E_{a,i}/RT)$$

wherein $k_i(T)$ is the rate coefficient [units: $s^{-1}$] at temperature T [units: K],
$A_i$ is the pre-exponential factor [units: $s^{-1}$],
$E_{a,i}$ is the activation energy [units: J/mole], and
R is the gas constant[=8.314 J/(Kmole)].

Examples of rate processes are: epithelial damage (i=1) and stromal modification (i=2); both i=1 and 2 can be overall rate processes that include many individual processes; a "rate-determining step" can govern the overall rate. These rate processes have small rate coefficients $k_i(T)$ at low T, with a "threshold" equal to activation energy $E_{a,i}$ but rate coefficients increase exponentially with increasing T, leading to exponential amplification of temperature difference effects. All corneal stromal thermal rate processes pertinent to this invention including, but not limited to, thermal damage and thermochemical processes have overall rate coefficients that can be represented in Arrhenius equation form.

Figure 5:
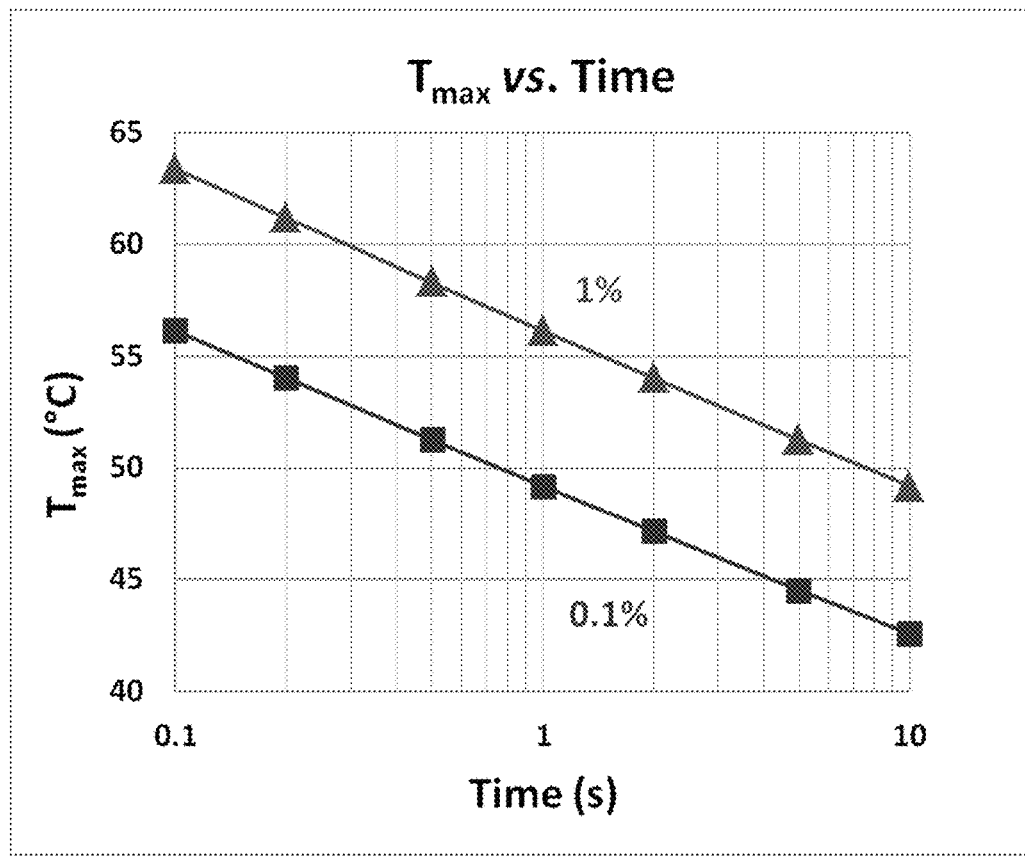
FIG. 5: $T_{max}$ required to achieve 0.1% thermal damage (squares) or 1% thermal damage (triangles) as a function of time at $T_{max}$. The logarithm (base 10) of time is plotted on the abscissa.

Each corneal vitrification rate process is a kinetic process; the extent to which each process occurs depends on its thermal history (i.e., the detailed temperature vs. time treatment). Each process does not occur instantaneously when $T_{max}$ is achieved by heating, but instead is governed by the Arrhenius rate coefficient for that process. The extent of the process (the "percentage conversion" from constituent A to constituent B, B to C and so on) is different for fast heating/short heating duration conditions in which the cornea is heated to each $T_{max}$ rapidly and then remains at $T_{max}$ for a short duration (for example, within a 1 second period) compared to slow heating/long heating duration conditions. Typically, the faster the heating (and the shorter the overall duration of the heating), the greater $T_{max}$ must be to produce the same transformation percentage conversion. FIG. 5 shows example values of $T_{max}$ that are required to achieve 0.1% and 1% conversion for heating durations between 100 milliseconds and 10 seconds; the example Arrhenius parameters are selected to be: $A=3.0\times10^{44}$ $sec^{-1}$, $E_a$=293 kJ/mole. These example parameters are thermal damage parameters for nonstromal cellular necrosis. (Noncellular thermal damage parameters pertain to noncellular corneal damage processes that occur principally at higher temperatures for the same heating duration compared to cellular necrosis.) As an example, if the fast heating duration at $T_{max}$ is 1 second, $T_{max}$ can be 49.2° C. if 0.1% thermal damage is acceptable but can be a greater $T_{max}$ of 56.2° C. if 1% thermal damage is acceptable (and 63.4° C. if 10% thermal damage is acceptable—not shown in FIG. 5). In addition, the process percentage conversion values in FIG. 5 are strict upper limits since only the center of the heat affected zone (HAZ), with a small volume contained within r,θ,z coordinates, is heated to $T_{max}$; other portions of the HAZ are heated to temperatures less than $T_{max}$. Because rate processes occur with rate coefficients that increase exponentially with increasing T, treatment occurs predominantly in a treated volume ($V_{TX}$) at, or within a few degrees of, $T_{max}$. In the instant invention, $V_{TX}$ is defined to be the volume treated at temperatures between $T_{max}$ to $T_{max}$-5° C. In some embodiments, the inventive system includes a result, wherein the result can be a corneal modification, wherein the corneal modification can be a corneal vitrification, wherein the corneal vitrification can be maximized, and wherein deleterious effects including, but not limited to, thermal damage can be minimized. In some embodiments, the Arrhenius parameters for processes, as well as the direct measurement of both targeted beneficial effects and unwanted deleterious effects, can be determined.

In some embodiments, the range of thermal damage (i.e., cellular necrosis due to heating) to each in vivo corneal structure within each treated volume including, but not limited to, the corneal basal epithelium is limited to thermal damage between 1% to 50%. In some embodiments, the maximum temperature $T_{max}$ produced within the corneal basal epithelium and anterior basement membrane includes, but is not limited to, $T_{max}$ between 40° C. to 75° C. for a range of thermal history between 20 milliseconds (ms) to 2000 ms. In all cases, $T_{max}$ depends on the duration of heating.

Figure 6:
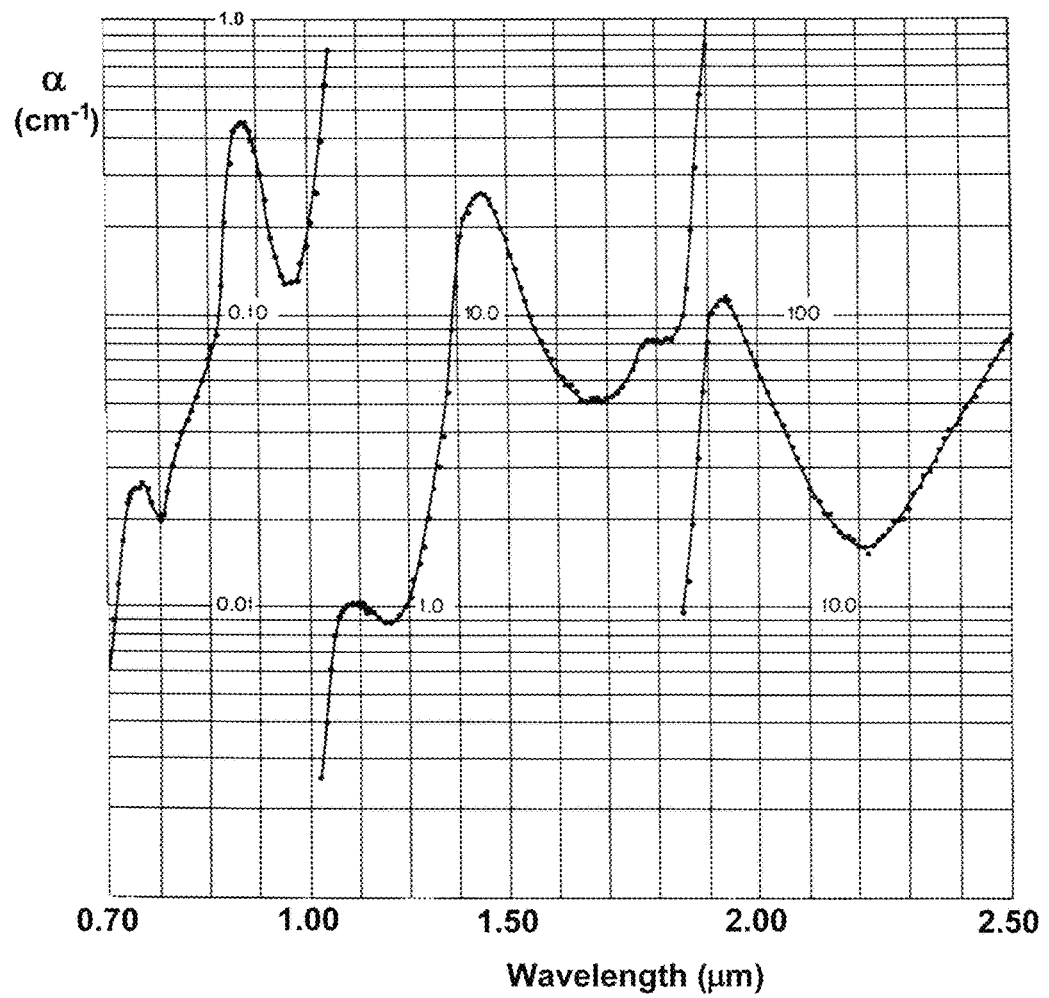
FIG. 6: Liquid water absorption coefficients at room temperature in the 0.70 to 2.50 μm spectral region.
Figure 7:
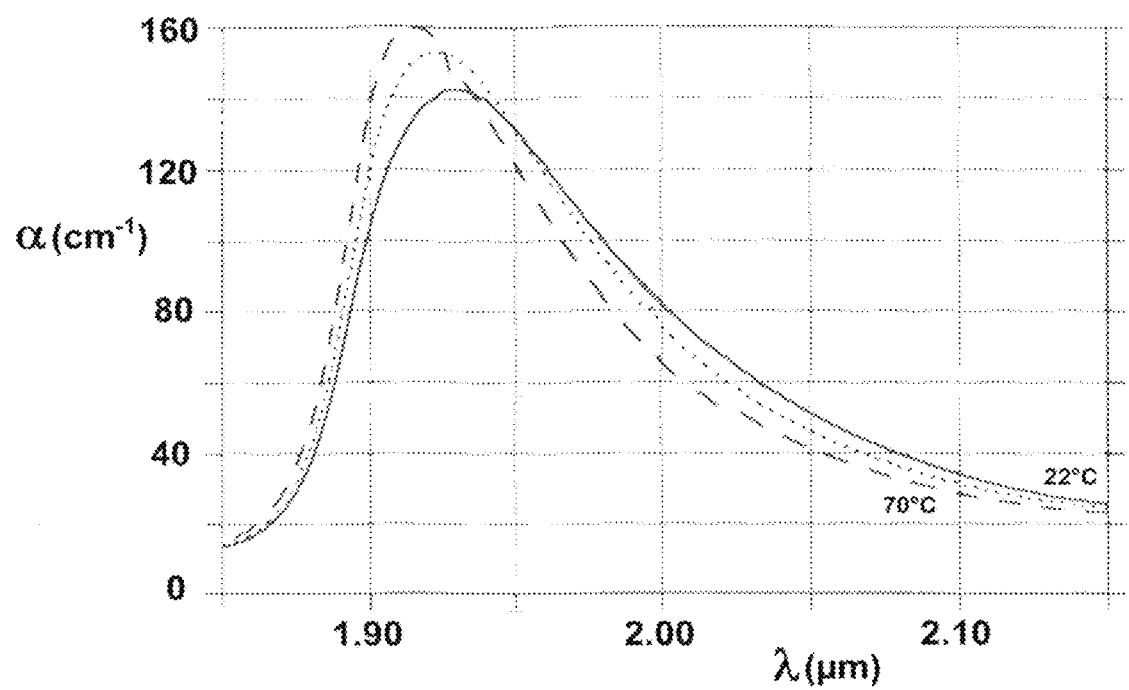
FIG. 7: Liquid water absorption spectra at 22° C. (solid line), 49° C. (dotted line) and 70° C. (dashed line).
Figure 8:
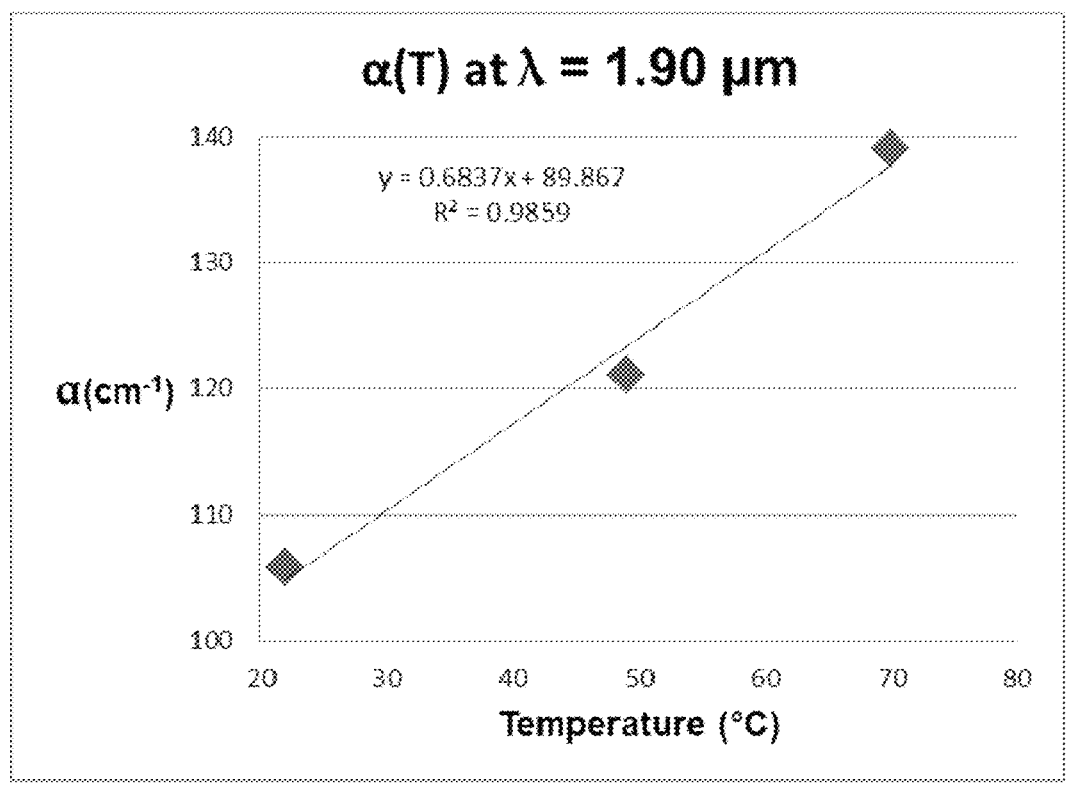
FIG. 8: Liquid water absorption coefficients at 1.90 μm wavelength at 3 temperatures. A linear regression data fit is shown.

In some embodiments, a system for vitrification of at least one treated volume of corneal stromal tissue of an in vivo human cornea of an in situ eye is used for modification of corneal structure and corneal properties, including, but not limited to, modification of corneal elastic modulus, corneal optical aberrations, adhesion of apposed stromal tissue, including but not limited to, after corneal wound closure; adhesion of donor transplanted corneal stromal tissue or synthetic implanted material to apposed host donor stromal tissue, or any combination thereof. In some embodiments, a system for vitrification of at least one treated volume of corneal stromal tissue of an in vivo human cornea of an in situ eye is based on at least one photon source that is configured to generate at least one photon output containing at least one photon wavelength corresponding to a liquid water absorption coefficient (α) at room temperature (T; ca. 20° C.) that is in a range between 20 and 300 $cm^{-1}$. FIG. 6 shows absorption spectra (i.e., absorption coefficient α vs. photon wavelength) of liquid water at room T in the 0.7 to 2.5 μm spectral region. Absorption coefficients in FIG. 6 are given on three separate logarithmic scales for three wavelength regions; water as between 20 and 300 cm$^{-1}$ are available at long wavelength between ca. 1.41 to 1.49 μm, between ca. 1.86 to 2.14 μm and between ca. 2.28 to 2.50 μm, as well as at wavelengths longer than 2.50 μm that are not shown in FIG. 6. FIG. 7 shows absorption spectra of liquid water at room T (22°) and at two elevated temperatures (49° C. and 70° C.); at wavelengths shorter than ca. 1.93 μm, the water α increases as a function of increasing T whereas, at wavelengths longer than ca. 1.93 μm, α decreases as a function of increasing T. As an example, FIG. 8 shows the temperature dependence of the water α at 1.90 μm wherein T-dependent as are measured from FIG. 7 and a linear fit to α vs. T measurements is shown. In some embodiments of this invention, at least one photon output containing at least one photon wavelength between ca. 1.86 to 1.93 μm is used for modification of corneal structure and corneal properties, including but not limited to corneal elastic modulus and corneal optical aberrations, or for adhesion of apposed stromal tissue, including but not limited to, after corneal wound closure; adhesion of donor transplanted corneal stromal tissue or synthetic implanted material to apposed host donor stromal tissue or for any combination thereof in order to use the increase of water α as a function of increasing T. In some embodiments of this invention, at least one photon output containing at least one photon wavelength between ca. 1.93 to 2.14 μm is used for modification of corneal structure and corneal properties, including but not limited to corneal elastic modulus and corneal optical aberrations, or for adhesion of apposed stromal tissue, including but not limited to, after corneal wound closure; adhesion of donor transplanted corneal stromal tissue or synthetic implanted material to apposed host donor stromal tissue or for any combination thereof in order to use the decrease of water α as a function of increasing T.

It should be noted that, throughout the 0.7 to 2.5 μm spectral region shown in FIG. 6, water is the dominant chromophore for tissue absorption, so the instant invention uses cornea absorption coefficients in this region based at least in part on the amount of water contained in cornea. At longer wavelengths than 2.5 μm, in the mid-infrared spectral region, non-water components of the cornea typically have substantial absorptions. Since water is the dominant absorber in the 0.7 to 2.5 μm spectral region shown in FIG. 6, the cornea absorption coefficient αcornea is approximately given by:

$$\alpha cornea = \alpha water \, mfwater \, \rho cornea / \rho water \quad \text{Eqn. 1}$$

wherein αwater is the liquid water absorption coefficient, mfwater is the mass fraction of water in the cornea, ρcornea is the density of the cornea, and ρwater is the density of water (0.9978 at T=20° C.).

The mass fraction of water in the cornea mfwater depends upon cornea hydration (which typically varies from anterior to posterior, from superior to inferior, diurnally, etc.), but is approximately 0.75 for the anterior stroma and 0.79 for the posterior stroma. Typically, the density of the cornea ρcornea is ca. 5% larger than that of water. In some embodiments, assuming that the ratio of densities ρcornea/ρwater remains constant as a function of temperature over the T=20° C. to 80° C. range, the instant inventions utilize the following approximate equation (2):

$$\alpha cornea, T = ca. \, 0.8 \, \alpha water, T \quad \text{Eqn. 2}$$

In the 1.8 to 2.2 μm spectral region shown in FIG. 7, the shape of the room temperature T (ca. 20° C.) absorption spectrum of cornea is the same as that of water. In some embodiments, in the 1.8 to 2.2 μm spectral region, cornea a values over the T=20° C. to 80° C. range can be approximated as being 80% of water α values. In some embodiments, if cornea tissue has previously received vitrification treatment, including but not limited to photovitrification treatment, its water content can be changed; for example, the anterior stroma can have reduced water content and hence a reduced absorption coefficient. In some embodiments, the thermal history during a repeated photovitrification treatment can differ from that during a previous photovitrification treatment because a change of corneal water content will change the absorption coefficient, the heat capacity, and the thermal diffusivity of the corneal tissue. In some embodiments, there may also be dynamic water absorption effects including a reduction in water content within the photovitrification (PV) heat affected zone (HAZ) that is accompanied by a reduction in absorption coefficient, both of which occur during a photovitrification treatment pulse and/or pulse sequence.

In some embodiments, the range of water absorption coefficients (αs) at room temperature (T; ca. 20° C.) includes, but is not limited to, αs between 20 and 300 cm$^{-1}$. In some embodiments, the range of photon wavelengths includes wavelengths at which the water absorption coefficient in a range between 20 and 300 cm$^{-1}$.

In some embodiments, the instant invention utilized its methods in conjunction with its devices for corneal vitrification, comprising vitrification of at least one treated volume of in vivo corneal stromal tissue formed within the naturally occurring corneal stromal tissue of an in vivo cornea of an in situ eye that can be used to modify the structure and properties, including but not limited to corneal elastic modulus and corneal optical aberrations of an in vivo human cornea of an in situ eye. In some embodiments, vitrification within the treated stromal tissue volumes increases the magnitude and duration of modification of corneal structure and corneal properties, including but not limited to corneal elastic modulus and corneal optical aberrations.

In some embodiments the instant invention utilizes its methods in conjunction with its devices, which produce photons to modify in vivo corneal stromal tissue, wherein the treated volume comprises corneal stromal tissue treated in the temperature range between the maximum temperature $T_{max}$ to a lower temperature $T_{max}$-5° C.

In some embodiments, photovitrification (PV) heat affected zones (HAZs) are produced by fast heating of in vivo corneal stromal tissue of an in vivo cornea of an in situ human eye during a 100 millisecond laser irradiation in which a peak temperature increase of approximately 50° C. is produced, corresponding to a heating rate of approximately 500 degrees (° C.) per second. In some embodiments, similar HAZs are produced in in vivo corneal stromal tissue of in vivo corneas of in situ human eyes by fast heating within HAZs using energy sources that produce heating rates between 5° C./s and 20000° C./s for a period of time, typically with one or more heatings each within a time duration of 20 to 2000 milliseconds, that provides the thermal history required to increase vitrification of treated corneal stromal tissue and to minimize deleterious effects including, but not limited to, thermal damage (i.e., non-stromal cellular necrosis due to heating). Since heating effects on the corneal stroma and other corneal structures are all produced by kinetic phenomena, typically with rate coefficients that can be represented by the Arrhenius equation (as described above), it is necessary to control not only the maximum heating (to a maximum temperature $T_{max}$) but also to control the thermal history in order to achieve targeted beneficial heating effects, including vitrification, and also to minimize unwanted deleterious effects. The optimal thermal history is designated herein by the term "moderate temperature fast heating".

In some embodiments, the instant invention produces moderate temperature fast heating effects that maximize beneficial in vivo corneal stromal changes including vitrification and that minimize deleterious effects by a judicious selection of maximum (but moderate) temperature and fast heating rate. The combination of $T_{max}$ and the duration of heating at $T_{max}$ can be selected by specifying the upper limit to the amount of deleterious effects, including the percentage thermal damage, and then restricting the thermal history of heating, including the combination of $T_{max}$ and the duration of heating at $T_{max}$, to produce no more than the upper limit of deleterious effects. For example, FIG. 5 can be used to select the moderate temperature fast heating conditions that restrict thermal damage to 0.1% or 1% of HAZ volume.

In some embodiments, the instant invention is directed to devices that utilize photons to irradiate in vivo corneal stromal tissue of an in vivo cornea of an in situ human eye to produce vitrification that remains in a persistent vitrified condition at physiological temperature after vitrification treatment has been completed. In some embodiments, the PV devices are configured to exhibit irradiation characteristics, such as, but are not limited to, wavelength(s), irradiances, and their spatial distribution(s) and time-dependent distribution(s) so as to provide increased targeting of beneficial modification of the anterior stroma together with increased minimization of deleterious effects to corneal structures. In some embodiments, the PV devices are non-laser devices configured to exhibit intense pulsed light (IPL) irradiation characteristics such as, but are not limited to, wavelength distribution, spectral irradiance(s), and their spatial distribution(s) and time-dependent distribution(s).

In some embodiments, as detailed herein, the PV devices of the instant invention are utilized in conjunction with an accessory device, which applies external stress to the anterior surface of the cornea during the corneal vitrification treatment. The accessory device, a reverse template (impression die) applies pressure to at least one vitrification treated volume of the the in vivo corneal stromal tissue of an in vivo cornea of an in situ eye. The reverse template further densifies stromal tissue of the vitrification treated volume of an in vivo cornea of in situ eye through an external stress, wherein the external stress is associated with an enhancement of at least 5% in stromal density within the at least one treated volume of the in vivo corneal vitrified stromal tissue of an in vivo cornea of an in situ eye. The reverse template provides external stress to vitrification treated volumes of the cornea in order to increase targeted beneficial effects while minimizing deleterious effects, including but not limited to, for example, thermal damage.

In some embodiments, the range of heating duration includes, but is not limited to, heating duration between 20 to 2000 milliseconds. In some embodiments, the range of heating rate includes, but is not limited to, heating rate between 5° C. per second to 20000° C. per second.

In some embodiments, a system for corneal stromal tissue photovitrification (PV) of at least one treated volume of corneal stromal tissue is used for modification of corneal structure and corneal properties, including but not limited to corneal modulus and corneal optical aberrations, or for adhesion of apposed stromal tissue after corneal wound closure; adhesion of donor transplanted corneal stromal tissue or synthetic implanted material to apposed host donor stromal tissue, or for any combination thereof of an in vivo human cornea of an in situ eye; said system comprises several components including: A—at least one photon source, B—an optical fiber delivery subsystem and C—an ocular fixation device. The components are specified as follows:

A—At least one photon source is configured to generate at least one photon output containing at least one photon wavelength corresponding to a liquid water absorption coefficient at room temperature (ca. 20° C.) that is in a range between 20 and 300 cm$^{-1}$. The at least one photon output is also configured to comprise a single photon pulse, a sequence of photon pulses, or any combination thereof, wherein each pulse has a predetermined time-dependent waveform containing a pulse energy within a time window of 20 to 2000 milliseconds, in which multiple pulses are separated by time periods of 10 to 200 milliseconds.

B—An optical fiber delivery subsystem that comprises:
at least one optical fiber configured to generate a predetermined photon output energy within each treatment area,
optics and/or spacers associated with the at least one optical fiber distal end, said optics and/or spacers to generate a predetermined photon output energy within each treatment area,
shaped and/or combined distal ends of the at least one optical fiber, such shaped distal ends comprising non-circular cross-sections including elliptical and stadium in shape with flat distal surfaces, circular cross-sections with curved distal surfaces and such combined distal ends with flat distal surfaces including combined distal ends with partial circular cross-sections and at least one flat side that are combined on their flat sides, or any combination thereof,
wherein the photon output energy is in the range of 20 to 1000 millijoules (mJ) [at the at least one wavelength at which the water absorption coefficient at room temperature (ca. 20° C.) is in a range between 20 and 300 cm$^{-1}$] per pulse per treatment area;
wherein the optical fiber delivery subsystem is configured to deliver the at least one predetermined photon output energy into an ocular fixation device; wherein the optical fiber delivery subsystem is configured to deliver the at least one predetermined photon output energy onto an optical element forming part of the posterior structure of the ocular fixation device, said optical element composed of a thermally conductive optical material in contact with the anterior corneal surface, the said predetermined photon output energy to be delivered through said optical element onto at least one treatment area on the cornea, said area in the range of 0.2 to 100 mm$^2$;
wherein the shape of each treatment area has a shape selected from the group consisting of: circular, overlapping circular, elliptical, oval, stadium, polygonal, polygonal with rounded corners, arcuate, annular, or any combination thereof; wherein one or more treatment areas is organized in a treatment (Tx) geometrical arrangement centered on the pupil centroid (or another centration reference such as the coaxially sighted corneal light reflex), wherein the shape of the Tx geometrical arrangement is selected from the group consisting of:
i) an axisymmetric geometrical arrangement, comprising a group of even number-fold (2, 4, 6, 8, 10 or 12) of treatment areas;
ii) an asymmetric geometrical arrangement, comprising a group of odd number-fold (1, 3 or 5) treatment areas; or
iii) any combination thereof;

wherein each circular treatment area center is located at predetermined polar (r,θ) coordinates;
wherein noncircular treatment areas have geometric references selected from the group:
overlapping circle centers, axes, apices, arcuate lengths and widths, or annular widths, said geometric references located at predetermined polar (r,θ) coordinates;
wherein the optical fiber delivery subsystem is configured to produce smooth (see below), low magnitude corneal curvature gradients between and within at least one of the following: angular segments, radial segments, or any combination thereof;
wherein corneal curvature gradients are between 0.1 to 3 diopters (D)/mm;
wherein the optical fiber delivery subsystem is configured to be mounted on the ocular fixation device;
C—The ocular fixation device,
wherein the ocular fixation device is configured to deliver the at least one predetermined photon output energy to at least one treatment area on the in vivo human cornea of the in situ eye,
wherein the ocular fixation device comprises:
a suction ring assembly and
an optical element in contact with the corneal anterior surface,
wherein the optical element is composed of a thermally conductive optical material that is sufficiently designed to be:
substantially transparent to the at least one photon output,
planar on the optical element surface in contact with the corneal anterior surface, and
sufficiently thermally conductive and sufficiently sized to provide a temperature within ±5 degrees from a physiological cornea surface T (approximately at 35° C.) during photovitrification treatment. In some embodiments, the optical element in contact with the anterior corneal surface can consist of, but is not limited to: sapphire (chemical composition:
$Al_2O_3$), infrasil quartz (a type of low-OH quartz that is substantially transparent), diamond or any combination thereof. In some embodiments, the optical element in contact with the anterior corneal surface can have high optical quality so that photons are transmitted through it without substantial scattering. In some embodiments, at least a part of the optical element of the ocular fixation device including: the proximal surface (not in contact with the cornea), the body of the optical element, the distal surface (in contact with the anterior surface of the cornea), or any combination thereof can provide substantial photon scattering in order to: expand the photon spatial distribution to enlarge the treatment (Tx) area, diffuse the photon spatial distribution to "homogenize" the photoirradiation over the Tx area, or any combination thereof.

In some embodiments, the optical fiber delivery subsystem) can be configured to be separate from the ocular fixation device and accessory optics, together with an eye tracking system, can be used to position photon outputs on treatment (Tx) area locations on the cornea.

In some embodiments, the ocular fixation device can be configured with a plano-concave optical element that is mounted on the cornea using a suction ring assembly, wherein the concave surface of the optical element is in contact with the anterior surface of the cornea.

In some embodiments, a system for modification of corneal structure and properties, including but not limited to, corneal elastic modulus, corneal optical aberrations, or for any combination thereof of the in vivo human cornea of the in situ eye is configured not to prevent a corneal wound healing response but, instead, to primarily reduce mainly deleterious corneal wound healing effects.

In some embodiments, a system for modification of corneal structure and properties, including but not limited to corneal elastic modulus, corneal optical aberrations, or for any combination thereof of the in vivo human cornea of the in situ eye is configured to produce a predetermined individual photon output energy for irradiating each treatment area on the surface of the cornea so as to produce spatial thermal histories that cause predetermined corneal stromal changes resulting in vision improvement; and wherein the system for modification of corneal optical aberrations, for modification of corneal structure and properties, or for any combination thereof the in vivo human cornea of the in situ eye is configured to form predetermined treatment areas, shapes and geometrical arrangements selected to affect at least one of the following: at least one lower order optical aberration, at least one higher order optical aberration, at least one optical aberration that is not described predominantly (at least 51%) by Zernike polynomials (and coefficients) up to and including $8^{th}$ radial order, or any combination thereof. In some embodiments, the optical aberration can include a corneal optical aberration, a lenticular optical aberration, or any combination thereof.

In some embodiments, the at least one photon source is a semiconductor diode laser that produces at least one photon output. In some embodiments, the at least one photon source is a solid-state laser doped with at least one ion that produces at least one photon output. In some embodiments, the at least one photon source is an intense pulsed light source comprising a flashlamp and its associated electrical energy storage and discharge electronics. In some embodiments, the at least one photon source is equipped with optical elements to provide wavelength selection and bandwidth narrowing of the photon output. In some embodiments, wavelength selection and bandwidth narrowing are provided by at least one of: optical transmission filters, optical reflection filters, optical diffraction filters, volume Bragg gratings, birefringent filters, diffraction gratings, prisms, or any combination thereof.

In some embodiments, a plurality of semiconductor diode laser photon outputs is directed so that each photon output is coupled directly into an individual fiber of the optical fiber delivery subsystem, wherein each of the plurality of photon outputs is individually controlled with respect to at least one output characteristic selected from the group consisting of: wavelength, output shape, time-dependent pulse distribution (i.e., pulse waveform) of each pulse, time-dependent pulse sequence in the case of multiple pulses, and energy of each pulse.

In some embodiments, the at least one photon output is a collimated or collected beam of photons that is configured to be directed so that each beam is:
i) focused directly into an individual fiber in the optical fiber delivery subsystem,
ii) split into two or more beamlets by an optical subsystem comprising at least one mirror, at least one beamsplitter, at least one focusing lens, at least one modulator, or any combination thereof, in which said beamlets are each coupled into individual fibers in the optical fiber delivery subsystem, or
iii) any combination thereof,
wherein each photon output (beam and/or beamlet) is individually controlled with respect to at least one of the following output characteristics selected from the group consisting of: wavelength, output shape, time-dependent pulse distribution (i.e., pulse waveform) of each pulse, time-dependent pulse sequence in the case of multiple pulses, and energy of each pulse wherein the at least one modulator is configured to modulate at least one characteristic of each photon output (beam and/or beamlet); and wherein the at least one modulator is selected from the group consisting of: iris diaphragm, variable transmission filter, shutter, or any combination thereof.

In some embodiments, the time-dependent pulse sequence is configured to stabilize modification of corneal structure and properties, including but not limited to corneal elastic modulus, corneal optical aberrations, corneal wound closure, adhesion of transplanted tissue or for any combination thereof of an in vivo cornea of an in situ eye comprising vitrification of at least one treated volume of corneal stromal tissue, said stabilization comprising lower temperature heating than was used to treat tissue initially. As an example, in some embodiments, at least one pulse can heat at least one treated volume to $T_{max}$ for a short duration of time and then at least one following pulse (or the continuation of the first pulse at lower irradiance) can heat the at least one treated volume to a temperature lower than $T_{max}$ for a longer duration of time than the first pulse. In some embodiments, the adhesion of joined portions of corneal tissue including, but not limited to, transplants of donor corneal buttons into host corneas can be increased by vitrification and stabilization of corneal stromal tissues in apposition. It is important to note that the vitrification and stabilization process described herein differs markedly from microwelding approaches that have previously been used to increase adhesion by "melting" collagen, including denaturation. The present invention involves "moderate temperature fast heating" that does not cause collagen melting.

In some embodiments, the optical fiber delivery subsystem comprises at least one of: one or more optical fibers, spacing elements, optical elements, electromechanical actuators, or any combination thereof configured to change treatment areas and treatment geometrical arrangements on an in vivo cornea of an in situ eye by changing the spacing of optical fiber distal ends, lenses, mirrors, prisms, or any combination thereof with respect to the anterior surface of the cornea. In some embodiments, the lenses are at least one of: spherical lenses, cylindrical lenses, Powell or other aspheric lenses, diffractive lenses, axicons, microlenses, or any combination thereof. In some embodiments, the mirrors are at least one of: flat mirrors, concave mirrors, aspheric mirrors, or any combination thereof. In some embodiments, the prisms are Dove prisms.

In some embodiments, at least one photon source is configured to modify the in vivo cornea of an in situ eye using an optical scanner. The photon source is configured to have suitable irradiation characteristics (comprising wavelength(s), time-dependent energy outputs, etc.), with an output beam that is focused by a long focal length lens, directed onto a scanning mirror mounted on a galvanometer that is configured to scan the beam onto a fiber array. In some embodiments, the components of the inventive devices with an optical scanner include some of the following:

1—a lens that yields a small diameter (ca. 100 to 200 µm) focused spot on optical fibers (typically 500 µm core diameter) located in the fiber array, 2—a mirror that is highly reflective at the photon wavelength(s), 3—a galvanometer with a fast positioning speed (less than ca. 1 ms from fiber to fiber in the fiber array), 4—a fiber array that contains from 1 to 16 optical fibers, 5—scan control electronics to drive the galvanometer, and/or 6—a computer module programmed to produce a predetermined step-and-hold sequence of beam positions.

In some embodiments, examples of galvanometer components that can be used in the inventive devices can include:

A—an optical scanner containing a single-axis galvanometer and position detector (both from Cambridge Technology, 125 Middlesex Turnpike, Bedford, Mass. 01730) such as Model 6210H together with a 3 mm aperture mirror mounted on the galvanometer motor, and B—a single-axis servo driver (e.g., Model 671 that is interfaced to computer control).

In an embodiment, the optical scanner can be programmed in a step-and-hold sequence that delivers predetermined irradiations of optical fibers in the fiber array. For example, for 8 fibers in a linear array, fibers 1 through 8 can separately receive 100 ms irradiations in a linear sequence or in a sequence such as 1-4-7-2-5-8-3-6 designed to "symmetrize" treatment (Tx) effects within an octagonal ring of 8 Tx areas per ring. In another embodiment, multiple irradiations of each fiber can be used for further symmetrization; for example, the 1-4-7-2-5-8-3-6 sequence can be used for 10 ms irradiations, followed by repeat sequences each with 10 ms irradiations, or some other sequences with 10 ms irradiations. In some embodiments, the purpose of "symmetrization" is to achieve equal Tx effects in each Tx area to prevent induced astigmatism.

In some embodiments, the present invention further includes a centration, out-of-plane orientation (i.e., tilt), and angulation aid to centrate and align the optical fixation device easily and accurately with respect to centration and angulation references and to reduce parallax error caused by tilt. In some embodiments, a reticle with a crosshair and angular markings is used to aid centration and angulation. In some embodiments, out-of-plane orientation (tilt) is reduced using a double reticle (with reticles spaced apart, with crosshairs that superimpose when viewed vertically downward when tilt is negligible), a bubble level indicator, or a combination thereof.

In some embodiments, the present invention further includes reverse template (impression die) projections on the optical element surface in contact with the anterior surface of the cornea, wherein said reverse template projections can produce modifications of the treated stromal volumes including but not limited to increased corneal stromal densification, increased vitrification and modification of corneal stromal mechanical properties, during photovitrification (PV) treatment. In some embodiments, the magnitude of the reverse template projections is in the range of 5 to 200 µm and the projections are located on the optical element to match the locations of PV treatment areas on the cornea. In some embodiments, the reverse template increases the effects of PV treatment including: the magnitude of corneal modification, the duration of corneal modification, vitrification or any combination thereof.

In some embodiments, the reverse template (impression die) is an impression solid comprising reverse template projections on the optical fixation device's posterior surface in contact with the anterior surface of the cornea; these projections provide external stress on the cornea during photovitrification (PV) treatment (Tx) and also are substantially equivalent to the optical element material in terms of optical and thermal properties. In the case of sapphire as the optical material of the optical element, wherein sapphire has a chemical composition $Al_2O_3$, the reverse template projections can be sapphire or any other material that can bond well to the sapphire substrate and that has similar optical properties as the substrate to transmit photon energy efficiently and similar thermal properties as the substrate to conduct heat away from the cornea efficiently during PV Tx. Sapphire reverse template projections on a sapphire optical element can also match (i.e., have similar values of) coefficients of thermal expansion as required for fine bonding under thermal cycling conditions. In some embodiments, the reverse template projections can have low photon scattering properties so that photons are transmitted through the optical element and through the reverse template projections without significant scattering. In some embodiments, the reverse template projections can have substantial photon scattering properties so that photons are transmitted without scattering through the optical element but are substantially scattered in propagation through the reverse template projections in order to: expand the photon spatial distribution to enlarge the treatment (Tx) area, diffuse the photon spatial distribution to "homogenize" the photoirradiation over the Tx area, or any combination thereof In some embodiments, the reverse template projections on the optical element can be produced by several suitable means including, but not limited to, laser machining/ablation, mechanical machining, chemical etching, chemical vapor deposition, physical vapor deposition, sputtering, bonding of ultrathin plates onto the optical element, or any combination thereof.

In some embodiments, in addition to the inventive devices, the instant invention further utilizes at least one of the following diagnostic instruments before, during and/or after treatments:

A—Corneal topography and tomography;
B—Optical coherence tomography (OCT) including epithelial thickness profiling;
C—Nonlinear microscopy, including second harmonic generation (SHG) imaging, third harmonic generation (THG) imaging and two-photon excitation fluorescence (TPEF) imaging to provide for complete analysis of epithelial, stromal-epithelial, stromal and endothelial effects;
D—Confocal microscopy;
E—Adaptive optics; and
F—Instrumentation suitable for measuring corneal mechanical properties (e.g., elastic modulus) including, but not only, Brillouin optical microscopy, quantitative ultrasound spectroscopy, corneal transient elastography, OCT elastography and atomic force microscopy.

In some embodiments, the range of each treatment (Tx) area on the cornea includes, but is not limited to, Tx area between 0.2 mm$^2$ to 100 mm$^2$. In some embodiments, the range of heated affected zone (HAZ) depth for each Tx area includes, but is not limited to, HAZ depth between 20 µm to 300 µm for each Tx area. In some embodiments, the range of photon source power includes, but is not limited to, power between 0.25 W to 20 W. In some embodiments, the range of photon output energy per pulse per Tx area includes, but is not limited to, energy between 20 millijoules (mJ) to 1000 mJ per pulse per Tx area. In some embodiments, the range of photon source duration per pulse includes, but is not limited to, photon source duration per pulse between 20 milliseconds (ms) to 2000 ms. In some embodiments, photon source waveforms include one or more than one pulse wherein the range of pulse separation in time includes, but is not limited to, pulse separations between 10 ms to 200 ms. In some embodiments, the range of thicknesses of projections on the reverse template includes, but is not limited to, thicknesses between 5 µm to 200 µm. In some embodiments, the range of changes to corneal optical aberrations include, but are not limited to, changes between 0.1 µm to 10 µm for each lower aberration, between 0.05 µm to 1.0 µm for each higher order aberration, and between 0.05 µm to 1.0 µm for each aberration that is not described predominantly (at least 51%) by Zernike polynomials (and their coefficients) up to and including 8$^{th}$ radial order. In some embodiments, the range of compensations for lenticular optical aberrations include, but are not limited to, compensation between 0.05 to 1.0 µm for each lenticular optical aberration.

In some embodiments of the instant invention, methods of use of devices and/or systems can be used in vivo cornea of an in situ human eye for corneal photovitrification (PV), for modification of corneal structure and properties, including but not limited to corneal optical aberrations, or for any combination thereof have at least the following example steps:

A—A drop of local anaesthetic (e.g., preservative-free proparacaine) is instilled into the eye.
B—After anaesthesia is effective, a drop of solute-free irrigant (e.g., distilled water) is instilled into the eye.
C—Following step B, an ocular fixation device, including its accessories (suction ring, optical element, conical holder and ring illuminator), is positioned over the eye.
D—Following step C, a crosshair reticle on the optical element is used for centration on the pupil centroid (or another centration reference).
E—Following step D, the cornea is applanated by the optical element by applying suction to the ocular fixation device suction ring between the cornea and the optical element with a pneumatic syringe.
F—Following step E, a handpiece that is part of an optical fiber delivery subsystem is docked onto the ocular fixation device using pre-aligned permanent magnets. The handpiece contains optical fibers that are pre-aligned in a pre-determined PV treatment (Tx) geometrical arrangement of, for example, two concentric rings with 4 or 8 fibers per ring.
G—Following step F, the cornea is photoirradiated over, for example, a 100 millisecond period in which PV Tx photons are delivered through the optical fibers. In some embodiments, each PV Tx area is irradiated for 100 milliseconds. During each irradiation, the corneal surface is kept within ±5 degrees from a physiological cornea surface T (approximately at 35° C.) during photovitrification treatment while the anterior corneal stroma is heated to produce photovitrification.
H—Following step G, the handpiece and ocular fixation device are removed from the eye.

Figure 9:
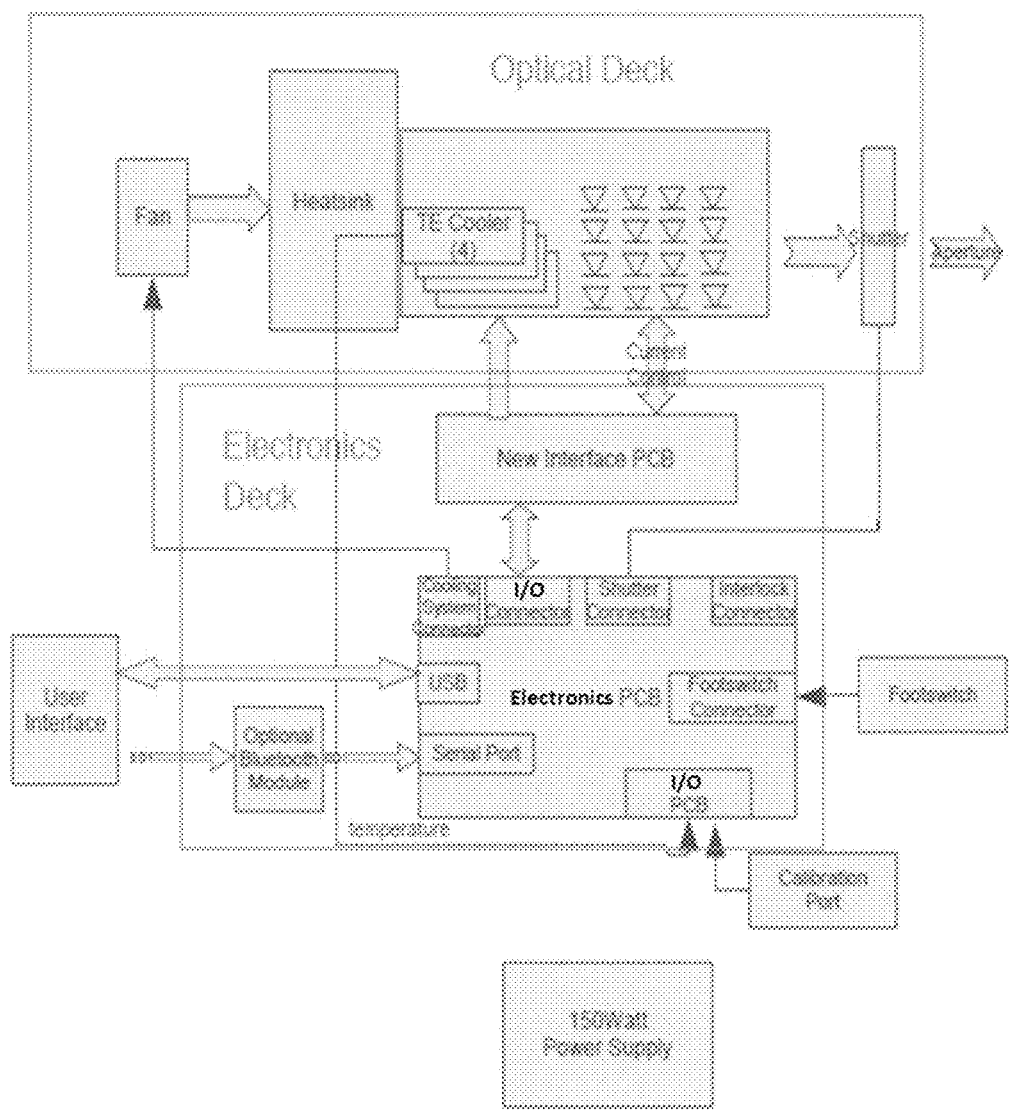
FIG. 9: Multiple photon source system used for photovitrification.

In some embodiments, the inventive devices of the instant invention can be configured, in accordance with the diagram of FIG. 9, so that at least two photon sources, as shown on the Optical Deck in FIG. 9, are independently controllable, wherein each photon source is individually coupled to an individual optical fiber in the optical fiber delivery subsystem. In some embodiments, the photon sources can be semiconductor diode lasers (SDLs) that are independently controllable. In FIG. 9, each SDL is symbolized as a diode. In FIG. 9, the following terms are used: PCB—printed circuit board, I/O—input/output, TE—thermoelectric, and USB—universal serial bus. In some embodiments, the inventive devices of the instant invention utilize at least 2 to 48 independently controllable photon sources that are individually coupled to individual optical fiber(s) in the fiber delivery system.

In some embodiments, a minimum of 1, 3, 5 or other odd numbers of independently controllable photon sources can be used. In some embodiments, vector components associated with providing symmetrical photoirradiation of a cornea (to reduce possible induced astigmatism) can be adjusted for odd-numbers of photon sources. In some embodiments, vector components can be adjusted for even-numbers of photon sources.

In some embodiments, the array of individual lasers is positioned on one or more common thermoelectric (TE) cooler plates that are used for thermal control; in FIG. 9, four TE cooler plates (one plate for each set of four SDLs) are shown In some embodiments, a shutter shown in FIG. 9 is used to change the duration of laser irradiation of the cornea when the SDLs are used in a cw mode continuously. In some embodiments, instead of utilizing the shutter, the inventive devices of the instant invention use the SDLs in a pulsed mode in which either the SDLs are inactive until activated by pulsed electrical current (i.e., "on/off" switching). In some embodiments, instead of utilizing the shutter, the inventive devices of the instant invention use the SDLs in a pulsed mode in which SDLs are in "simmer mode" (active but below the current threshold at which laser action occurs) and are then boosted above threshold by pulsed electrical current. In some embodiments, instead of utilizing the shutter, the inventive devices of the instant invention use the SDLs in a variable pulsed mode in which one or more SDL power outputs have predetermined waveforms including a variable waveform that has at least one of the following variations: "ramping up" the instantaneous power over the duration of the irradiation, maintaining a constant instantaneous power over the duration of the irradiation, and controlling a more complicated output of instantaneous power over the duration of the irradiation.

In some embodiments of the inventive devices of the instant invention, a beam from each photon source of a plurality of photon sources is directly coupled into its corresponding optical fiber and the characteristics of the coupled beam are modulated by the operational characteristics of the photon source itself In some embodiments of the inventive devices of the instant invention, a beam from each photon source of the plurality of photon sources is further passed through at least one optical system (e.g., lenses, mirrors, etc.) that further modulates at least one characteristic of the beam before the beam reaches its corresponding optical fiber. In some embodiments, an independent control of pulse durations in each photon source can also generate treatments to at least reduce astigmatism and other corneal disorders including, but not limited to, keratoconus, other naturally occurring ectasias and iatrogenic ectasias.

In some embodiments, the inventive devices of the instant invention at least include a microprocessor control board subsystem linked by universal serial bus (USB) to a laptop computer (or, optionally, to a tablet PC, iPad or smartphone) based user interface (UI). In some embodiments, the inventive devices of the instant invention can utilize a microprocessor board (MB) with an attached custom-designed interface board (IB). In some embodiments, the MB-IB control subsystem controls all of the photon sources, controls the internal shutters (if necessary) and/or any additional interlocks, mediates and/or oversees the firing of the photon sources, and/or controls and supervises the DC power from a power supply to provide electrical power to the photon sources. In addition, in some embodiments, the MB-IB subsystem controls, coordinates, and verifies calibration of photon outputs. In some embodiments, the inventive devices of the instant invention at least include a counter/enablement subsystem that registers patient photovitrification (PV) treatments (Txs), distinguishes PV Txs from calibration shots and enables prepaid and/or billed PV Txs.

In some embodiments, the inventive devices of the instant invention at least include software driven User Interface (UI). In some embodiments, the UI receives inputs from operators through a keyboard, touch screen panel and/or voice recognition software. In some embodiments, the UI not only provides the user settings for the photovitrification (PV) system, but also gives password protection for the user, logs and/or archives data, and/or provides technical diagnostics and/or real-time information for operation and maintenance of the system. In some embodiments, the UI uses patient ocular measurements to determine patient treatment requirements, including, but are not limited to, acquisition, tracking and pointing of ocular image data for mounting an ocular fixation device, and/or for specifying and controlling photon source energy delivery to each optical fiber in the optical fiber delivery subsystem that generates at least one PV treatment.

In some embodiments, the User Interface (UI) is in a form of a touchscreen control UI that connects to the microprocessor board via cable-linked, wireless universal serial bus (USB) and/or Bluetooth accessory and/or connects to the Internet. In some embodiments, communications includes uploading of patient records and/or videos (following compression if necessary) to a network server and/or downloading of software updates and information from the network server. In some embodiments, the inventive devices of the instant invention allow separating the user interface from the main processor, thus the tasks for setting procedure protocols and/or data archiving are isolated from the direct operations of the inventive devices.

In some embodiments, the inventive devices of the instant invention reduce cost and reduce system complexity. In some embodiments, since discrete photon sources can have individual output power monitoring, as well as individual correlated-channel control and monitoring at the distal end of the optical fiber delivery subsystem, the system calibration and resultant optical "dose" delivery to the patient is made more precise and more reproducible by the inventive devices of the instant invention. In some embodiments, the inventive devices of the instant invention allow to direct individual photon source energies to each photovitrification (PV) treatment (Tx) area, to at least affect (e.g., correct), reduce or alleviate/lessen the symptoms of astigmatism and other corneal disorders including, but not limited to, keratoconus, other naturally occurring ectasias and iatrogenic ectasias, as well as to compensate for naturally occurring and iatrogenic corneal epithelial thickness variations. In some embodiments, individual photon source energy (and/or timing) can adjust doses in each PV Tx area to overcome naturally occurring and iatrogenic epithelial thickness variation since such variation can be present pre-Tx and the variation can also change post-Tx, as has been observed for other laser vision modifying (e.g., optimizing) procedures. In some embodiments, the instant invention utilizes the data that considers epithelial thickness pre-Tx and as a function of time post-Tx. In some embodiments, the instant invention utilizes the data that considers photon source energy dosimetry delivered to the corneal stroma can be dependent on epithelial thickness; and thus can compensate for epithelial thickness variations by adjusting laser energy at each PV Tx area location. In some embodiments, the instant invention utilizes the data from optical and/or ultrasonic epithelial thickness profiling instruments to obtain epithelial thickness maps and to use epithelial thickness information to improve PV Txs.

In some embodiments, the inventive devices of the instant invention utilize direct coupling of each photon source to each optical fiber that allows reducing the number of mechanical and optical components. In some embodiments, the inventive devices of the instant invention allow for "drop-in" replacement of any photon source in the array. In some embodiments, the inventive devices of the instant invention allow for "drop-in" replacement of any optical fiber delivery subsystem.

Figure 10:
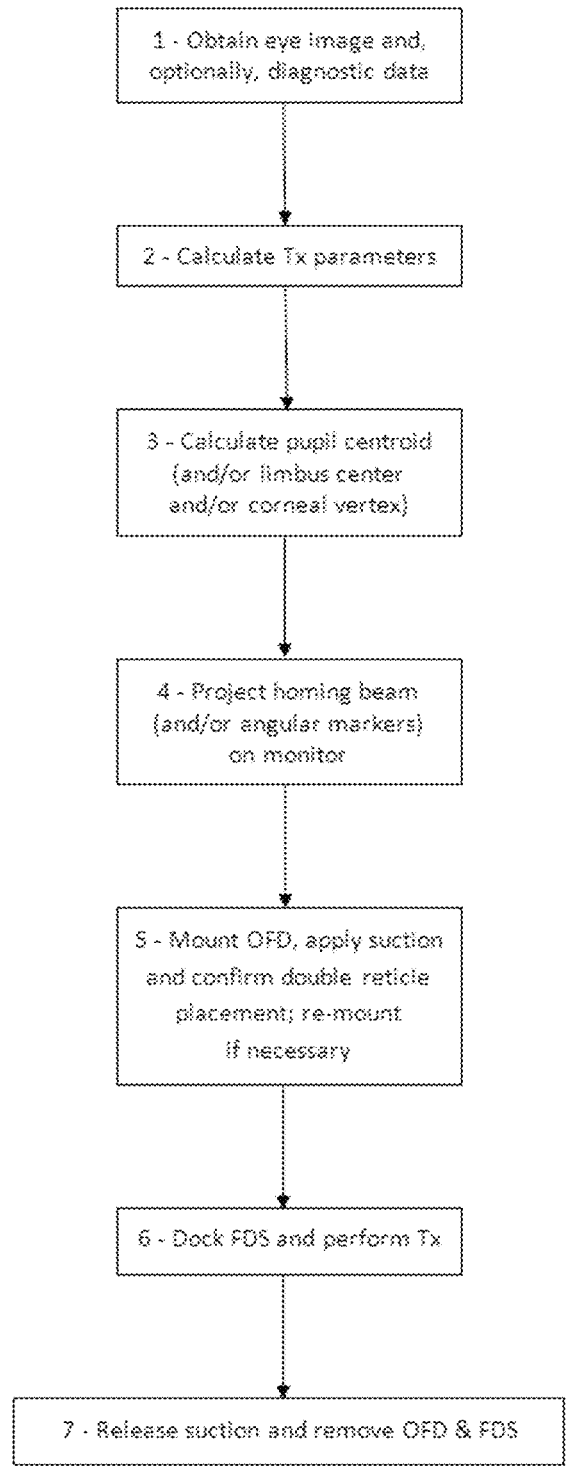
FIG. 10: Flow diagram of photovitrification (PV) treatment (Tx) procedure. Key: OFD—ocular fixation device, FDS—fiber delivery system

In some embodiments, the inventive devices of the instant invention are operated in the steps shown in FIG. 10. The patient initially views a fixation light that is located on the optical axis defined by a telescope line-of-view displayed on the center of a monitor of the inventive device (which is pre-aligned). In some embodiments, the fixation can be approximate; it is only necessary for the patient to look in a designated direction (e.g., along the optical axis). In some embodiments, the acquisition, tracking and pointing steps for centration, angulation, and normal incidence viewing are facilitated by a "homing beam" superimposed on the monitor to compensate for small displacements of the eye view from the optical axis.

In step 1 of FIG. 10 the eye image can be a real-time monitor display (on a screen of a computer portable device such as iPad3, a machine vision display, etc.) and, optionally, an imported image from a separate device; and diagnostic data can be imported from corneal topography, aberrometry, refraction, visual acuity and/or other measurements. In some embodiments, the separate imaging device is a camera that records the image of the eye.

In some embodiments, the inventive systems of the instant invention allow for monocular viewing with, for example, the iPad3 by using a telescope finder scope (such as, but is not limited to, the Orion Telescope black 6×30 right-angle correct-image finder scope which provides 6× magnification and has a 30 mm diameter objective lens with 7° field-of-view). In some embodiments, the suitable finder scope is mounted onto the iPad3 on the optical axis of the iPad3's camera. In some embodiments, a fixation light is also built into the suitable finder scope housing so that the patient eye fixates along the optical axis of the finder scope/camera. In some embodiments, the suitable finder scope is pre-aligned along the optical axis which then serves as a reference for fixation and for mounting the ocular fixation device assembly so that the optical axis is at normal incidence (e.g., perpendicular) to the optical element of the optical fixation device. In some embodiments, the parallax error (that could occur if the plane of the optical element surface of the ocular fixation device in contact with the cornea is not the same as the pupillary "plane") is eliminated by utilizing the monocular viewing, described above, plus the normal incidence geometry. In some embodiments, the inventive systems of the instant invention further include a double reticle and/or a level sensor that are used to verify/confirm the normal incidence viewing. In some embodiments, an equivalent centering system to the double reticle is used to verify/confirm the normal incidence viewing.

In step 2 of FIG. 10, photovitrification (PV) treatment (Tx) parameters are computed from diagnostic data; the inventive devices' characteristics (PV Tx energy and duration in each location) are adjusted automatically (using a PV Tx nomogram) to provide PV Tx parameters.

In step 3 of FIG. 10, for centration, the pupil edge is found in real-time at 4 or more semimeridians (for example, at 0°, 90°, 180° and 270°); the pupil centroid is the intersection of linear connectors between opposing semimeridians (for example, 0° and 180°). In some embodiments, the pupil centroid is a candidate centration reference onto which a "homing beam" can be projected on a monitor. In some embodiments, in step 3, other choices for centration reference can include the limbus center, the corneal vertex and the coaxially sighted corneal light reflex (CSCLR). In some embodiments, in step 3, other reference "markers" can be used for angulation such as, but are not limited to: iris patterns and scleral blood vessels. In some embodiments, angulation accuracy is necessary to treat symptoms of astigmatism. In some embodiments, the instant invention uses reference "markers" obtained in the supine position since ocular cyclotorsion occurs when a patient changes position from sitting upright to lying supine. In some embodiments, the inventive systems of the instant invention utilize pupillometry with edge detection which incorporates the following steps:

A—Video recording of the image of an eye, including the pupil and the limbus,

B—Application of an edge detection algorithm (such as the Canny edge detector) to locate pupil edges at a predetermined number of semimeridians (for example, at each integral semimeridian from 0° to 359°), C—Fitting of an ellipse to the array of edges and D—Location of the center point of the ellipse which is the pupil centroid.

The same procedure can be used to locate the limbus centroid by substituting the limbal edges for pupil edges in step B above.

In step 4 of FIG. 10, to aid the physician in mounting the ocular fixation device, the instant invention adds a "homing beam" (and angular markers in the case of at least reducing or alleviating/lessening the symptoms of astigmatism) to the monitor display. In some embodiments, the "homing beam" is displayed on the centration reference (such as the pupil centroid). In some embodiments, the reticle center—part of the ocular fixation device assembly—can be superimposed on the "homing beam" as viewed on the display. In some embodiments, angular markers on the ocular fixation device assembly can be superimposed on angular markers shown on the display.

In step 5 of FIG. 10, in some embodiments, the physician can mount the ocular fixation device assembly on the eye. In step 5 of FIG. 10, in some embodiments, machine vision is used to automate the mechanical placement of the ocular fixation device assembly on the eye. When the ocular fixation device assembly is properly mounted (with respect to centration, angulation and normal incidence—the latter verified by superposition of double reticle crosshairs or circles in order to reduce parallax error; as an alternative, an electronic level sensor can be used to verify that the optical element surface in contact with the cornea is at normal incidence to the optical axis), suction is applied. If the ocular fixation device assembly is not properly mounted, the suction can be released and the mounting steps can be repeated.

In step 6 of FIG. 10, in some embodiments, the optical fiber delivery subsystem is docked onto the mounted ocular fixation device assembly; a set of permanent magnets aligns the optical fiber delivery subsystem accurately with respect to the ocular fixation device. In some embodiments, the optical fiber delivery subsystem is docked manually by the physician. In some embodiments, the optical fiber delivery subsystem's docking is automated. Once docked, the photovitrification (PV) treatment (Tx) is performed. In some embodiments, PV Tx is initiated manually by the physician. In some embodiments, PV Tx is initiated automatically.

In step 7 of FIG. 10, in some embodiments, following the photovitrification (PV) treatment (Tx), suction is released and the ocular fixation device and optical fiber delivery subsystem are removed. In some embodiments, the step 7 is performed manually. In some embodiments, the step 7 is performed automatically.

In some embodiments, the inventive devices/systems of the instant invention allow to fully automate the entire procedure. In some embodiments, the inventive devices of the instant invention utilize machine vision and pattern recognition for acquisition, tracking and pointing of the centration, angulation and normal incidence references. In some embodiments, the inventive devices of the instant invention that utilize the ocular fixation device assembly "lock onto" the "homing beam" target and are mounted directly on target.

In some embodiments, once the ocular fixation device assembly is properly mounted, there are no requirements for acquisition, tracking and pointing; the magnet-to-magnet docking of the optical fiber delivery subsystem onto the ocular fixation device assembly provides accurate alignment of the photovitrification (PV) treatment (Tx) geometrical arrangement onto the cornea. In some embodiments, once the ocular fixation device assembly is mounted, small patient eye motion does not matter.

In some embodiments, the inventive alignment mechanisms/devices of the instant invention are designed to achieve centration for the specific photovitrification (PV) treatment (Tx) geometrical arrangements to obtain maximum and predictable utility of the inventive procedures utilizing the inventive devices of the instant invention. In some embodiments, the inventive devices of the instant invention utilize at least one of the following centration locations:

A—the pupil centroid (PC),
B—the corneal vertex (CV),
C—any other suitable centration reference location such as the coaxially sighted corneal light reflex (CSCLR) for patients with significant Angle Kappa.

Figure 11:
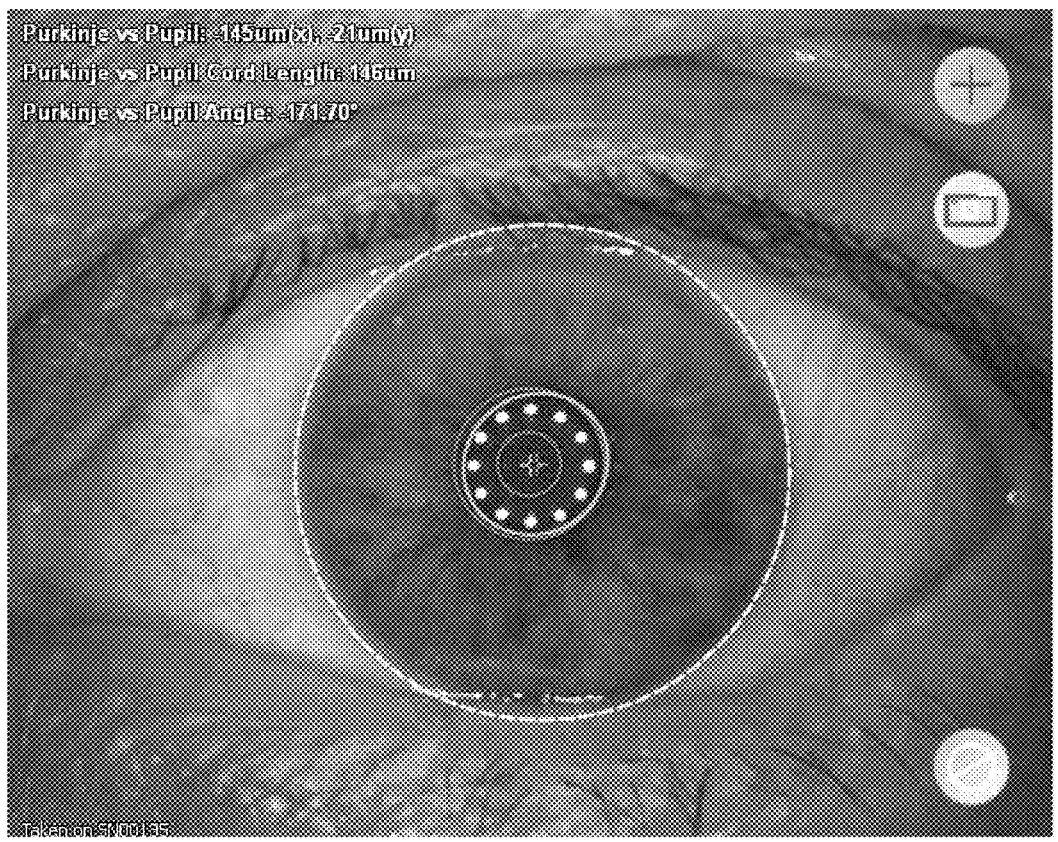
FIG. 11: Eye image with superimposed limbus and pupil edges together with centration references

In some embodiments, the inventive devices of the instant invention allow to mount them, such as an ocular fixation device, accurately and quickly, without repeated trauma to the cornea caused by multiple mounting attempts and/or excessive mounting adjustments. FIG. 11 shows an eye with the CSCLR (first Purkinje image; marked by a white cross) as the centration reference. The PC (under photopic illumination conditions; marked by a green cross that nearly overlaps the white cross) was displaced by X=0.145 mm, Y=0.021 mm from the CSCLR. The figure also shows computer-generated edge finding circles (yellow—limbus, green—pupil).

In some embodiments, the inventive devices of the instant invention allow to display a "homing beam" on the eye image on the pupil centroid PC, and/or on some other centration reference, to allow the physician to "home in" on his/her mounting target. In some embodiments, the pupil (or limbus) edges are not displayed as shown in FIG. 11. In some examples, a small number of pupil edge points (perhaps only 4 points at 0°, 90°, 180° and 270°) is sufficient to acquire in order to calculate the pupil centroid. In some embodiments, the "homing beam" on the PC is a flashing red light or another noticeable target.

In some embodiments, the inventive devices of the instant invention additionally utilize at least the following additional centration aids, but are not limited to:

A—a video camera and display with telescope together with a fixation light on the optical axis and at optical infinity,
B—guide circles on the video display that match ocular fixation device assembly image dimensions, and
C—a double reticle (one on or near the plane of the proximal face of the optical element of the ocular fixation device and the other at least 1 mm apart on the distal face of the optical element of the ocular fixation device) to prevent parallax errors—the spacing between reticles is as large as possible but does not exceed the depth of field of the telescope optics.

In some embodiments, the inventive devices of the instant invention allow to mount the ocular fixation device assembly accurately with respect to the angular orientation of the photovitrification (PV) treatment (Tx) geometrical arrangement in order to allow for sequential multiple PV Txs over time. For example, a patient can have a primary PV Tx that is followed by a secondary PV Tx at a later time. In some embodiments, the primary and secondary PV Tx geometrical arrangements do not overlap; for example, if the primary PV Tx geometrical arrangement includes PV Txs along the 0°-180° and 90°-270° meridians, the secondary PV Tx geometrical arrangement is oriented with PV Txs along the 45°-225° and 135°-315° meridians. In some embodiments, primary and at least one non-primary PV Tx can overlap substantially.

In some embodiments, accurate angulation at least affects (e.g., reduces or alleviates/lessens) the symptoms of astigmatism. In some embodiments, the instant invention accounts for one or more complicating factors such as cyclorotation of the eye that occurs when a patient lies down. In some embodiments, the inventive devices of the instant invention utilize iris registration to define the angular orientation in terms of fixed marks on the iris. In some embodiments, one or more secondary "homing beams" (in addition to the primary "homing beam" on the computer monitor or other centration reference) is included on the video display to aid the physician in mounting the ocular fixation device assembly accurately with respect to both centration and angulation.

In some embodiments, the inventive devices of the instant invention measure the location of the pupillary centroid, the corneal vertex, iris markers, etc. using diagnostic devices such as aberrometers or corneal topographers. In some embodiments, centration and angulation data then is transferred by software from diagnostic devices to some of the inventive devices of the instant invention for use in performing photovitrification (PV) treatment (Tx).

In some embodiments, use of suction is automated. In some embodiments, the automatic mounting of the ocular fixation device assembly can include optical detection of the meniscus edge formed by fluid located between the eye and the optical element of the optical fixation device; when the meniscus spreads sufficiently, an electronic control can start a predetermined amount of suction (such as 30 cm Hg pressure differential). In some embodiments, the inventive systems of the instant invention can utilize the edge-finding of the meniscus edge by the same or similar suitable type of procedure utilized in pupillometry as described above for pupillometry with edge finding.

In some embodiments, the inventive systems of the instant invention can utilize any other suitable systems/devices that optically detect/measure the meniscus without adding complexity and/or significantly increase (e.g., double) time of the inventing photovitrification (PV) treatment (Tx) methods.

In some embodiments, if the ocular fixation device assembly is not properly mounted, the suction can be released and the mounting steps can be repeated.

In some embodiments, the optical fixation device with a thermally conductive optical element in contact with the corneal anterior surface provides a temperature within ±5 degrees from a physiological cornea surface T (approximately at 35° C.) during photovitrification (PV) treatment Tx to improve accuracy and/or predictability of PV Tx. Typically, there is considerable patient-to-patient variability in ocular surface temperature. In some embodiments, the inventive treatments depend, at least in part, upon the thermal history of laser heating and, as a result, variations in an initial ocular (e.g., anterior corneal) temperature can alter PV Tx effects. The optical element of the ocular fixation device has sufficient thermal capacity and thermal diffusion between the cornea and is sufficiently efficient and fast to provide a temperature within ±5 degrees from a physiological cornea surface temperature (approximately at 35° C.) during photovitrification treatment.

In some embodiments, the inventive devices/systems of the instant invention provide a temperature within ±5 degrees from a physiological cornea surface temperature (approximately at 35° C.) during photovitrification treatment by measuring, continuously and/or periodically, the optical element temperature using one or more suitable techniques/devices such as a noncontact radiometer or other suitable device, wherein the T control device is a resistive heater or other suitable device that incorporates T measurements in a feedback loop for thermostated control of the temperature of the optical element of the optical fixation device in contact with the anterior corneal surface.

In some embodiments, the inventive devices/systems of the instant invention provide a temperature within ±5 degrees from a physiological cornea surface temperature (approximately at 35° C.) during photovitrification treatment by also incorporating measurements of variations in room temperature (typically, the room temperature varies from clinic to clinic and/or within a clinic from time to time).

In some embodiments, the inventive devices/systems of the instant invention utilize a feedback loop mechanism by, continuously or periodically, collecting, temperature measurements of at least one of: ocular surface temperature, optical element temperature, and room temperature; and based on the obtained measurement(s) adjusting the temperature of the optical element of the ocular fixation device by, for example, performing at least one of the following actions, but is not limited to: blowing warm air, resistive heating of the optical element of the ocular fixation device by, for example, using polyimide resistive heating tape that is in thermal contact with the optical element of the ocular fixation device, and other similarly suitable methods.

In some embodiments, the instant invention is directed to geometrical arrangements utilized to perform a photovitrification (PV) treatment (Tx) that uses photoirradiation to vitrify stromal tissue volumes of the cornea and modify cornea structure and properties, including but not limited to elastic modulus and optical aberrations—a method termed photovitrification keratoplasty (PVK). In some embodiments, the inventive geometrical arrangements of the instant invention can be utilized to correct or at least reduce hyperopia (aka farsightedness) by steepening the central cornea to increase its refractive power; to correct or at least reduce myopia (aka nearsightedness) by flattening the central cornea to decrease its refractive power; to correct or at least reduce symptoms associated with regular astigmatism and other corneal disorders including, but not limited to, keratoconus, other naturally occurring ectasias and iatrogenic ectasias, by axisymmetric and/or asymmetric PV Tx geometrical arrangements; and to alleviate/lessen the symptoms of age-related focus dysfunction by producing simultaneous visual acuity at multiple distances (near, intermediate and far) and increased depth of field. In some embodiments, as detailed below, the inventive geometrical arrangements of the instant invention can be utilized to minimize corneal epithelial remodeling. In some embodiments, specific Tx geometrical arrangements including, but not limited to, the Tx geometrical arrangements shown in FIGS. 12A through 12D, and 13 can be used for specific indications for use including, but not limited to, at least reduce hyperopia (FIGS. 12A, 12C and 13), to correct or at least reduce myopia (FIG. 12B and 12D), and to alleviate/lessen the symptoms of age-related focus dysfunction (FIGS. 12A through 12D, and 13).

In some embodiments, photovitrification (PV) treatment (Tx) areas, PV heat affected zones (HAZs), PV Tx geometrical arrangements and PV Tx conditions can be optimized for PV Tx applications including, but not limited to, reduction of ocular refractive errors of myopia, hyperopia and regular astigmatism; production of simultaneous near, intermediate and distance vision; reduction of irregular astigmatism and other corneal abnormalities including, but not limited to, keratoconus and other naturally occurring ectasias and iatrogenic ectasias; alteration of lower order aberrations (LOAs), higher order aberrations (HOAs), other aberrations that are not described predominantly (at least 51%) by Zernike polynomials (and coefficients) up to and including $8^{th}$ radial order; modification of corneal mechanical properties, or any combination thereof. In some embodiments, photovitrification (PV) treatment (Tx) areas, PV heat affected zones (HAZs) and the overall PV Tx geometrical arrangement are adjusted to match specific indications for use. In some embodiments, PV Tx conditions are adjusted with respect to not only PV Tx areas, PV HAZs and PV Tx geometrical arrangements, but also with respect to other parameters including, but not limited to, irradiation wavelength, output shape, time-dependent pulse distribution (i.e., pulse waveform) of each pulse, time-dependent pulse sequence in the case of multiple pulses, energy of each pulse, and the presence or absence of a reverse template. In some embodiments, PV Tx areas, PV HAZs, PV Tx geometrical arrangements and other PV Tx conditions are changed significantly for many reasons associated with, but not limited to: the type and magnitude of ocular optical aberrations; the type, magnitude and location of corneal disorders; the type (near, intermediate, far or any combination thereof) and magnitude of visual acuity improvement needed, the duration of effect, the type and magnitude of beneficial corneal stromal change to be maximized and the type and magnitude of unwanted deleterious side effects to be minimized.

In some embodiments, adjustments to the photovitrification (PV) treatment (Tx) areas include adjustments with respect to one or more of the following characteristics: size, shape, location (i.e., r,θ coordinates with respect to radial and angular references), orientation, gradients, smoothness, or any combination thereof; wherein corneal surface curvature gradients are reduced to 3 diopters (D) per millimeter (mm) or less(≤3 D/mm) and wherein smoothness is surface root-mean-square (RMS) roughness in each PV Tx area reduced to 10 µm or less. In some embodiments, all the PV Tx areas have the same characteristics of size, shape, location, orientation, gradients and smoothness in order to produce a symmetrical PV Tx. In some embodiments, at least one PV Tx area has different characteristics compared to other PV Tx areas in order to produce an asymmetrical PV Tx.

In some embodiments, photovitrification (PV) treatment (Tx) area size can be in the range of 0.2 to 100 mm² wherein the PV Tx area size refers to the corneal anterior surface area contained within the perimeter defined by the locus of full width at half maximum (FWHM) intensity ($I_{max,ave}/2$) points wherein $I_{max,ave}$ is the average maximum intensity [units: watts per square meter (W/m$^2$)] of the photon output within an output pulse. In some embodiments, at least one PV Tx area can have a shape selected from the group consisting of: circular, overlapping circular, elliptical, oval, stadium, polygonal, polygonal with rounded corners, arcuate, annular, or any combination thereof. In every case, the locus of $I_{max,ave}/2$ points defines the PV Tx area size. Since the cornea has a convex curved surface, the projection of a planar area onto the cornea has a larger area on the corneal surface.

In some embodiments, photovitrification (PV) treatment (Tx) area location and orientation, together with PV Tx geometrical arrangement, can be configured for modification of corneal structure and properties, including but not limited to corneal optical aberrations, corneal elastic modulus, or for any combination thereof that have beneficial effects including, but not limited to, reduction of ocular refractive errors of myopia, hyperopia and regular astigmatism; production of simultaneous near, intermediate and distance vision; reduction of irregular astigmatism and other corneal disorders including, but not limited to, keratoconus and other naturally occurring ectasias and iatrogenic ectasias; alteration of lower order aberrations (LOAs), alteration of higher order aberrations (HOAs), alteration of optical aberrations that are not predominantly (at least 51%) represented by Zernike polynomials (and their coefficients), modification of mechanical properties, or any combination thereof.

In some embodiments, devices and procedures for modification of corneal structure and properties, including but not limited to corneal optical aberrations, corneal elastic modulus, or for any combination thereof incorporate considerations of both acute (immediate) and delayed (including long-term) photovitrification (PV) treatment (Tx) outcomes in order to provide long-duration (over years) modification of corneal structure and properties, including but not only corneal optical aberrations, corneal elastic modulus or any combination thereof effects including, but not limited to, reduction of ocular refractive errors and other beneficial outcomes as listed above and also to provide optimal quality of binocular vision while eliminating or reducing clinically significant side effects including, but not limited to, induced ocular disturbances (e.g., night vision disturbances, glare disability, etc.) and induced ocular discomfort and dysfunctional tear syndrome. For example, in some embodiments, long-duration modification of corneal structure and properties, including but not limited to corneal optical aberrations, corneal elastic modulus or any combination thereof effects can be obtained, in part, by reducing regression of corneal structure and properties changes, including but not limited to corneal optical aberration changes, due to post-Tx epithelial remodeling (e.g., epithelial modification such as epithelial hyperplasia). Post-Tx epithelial modification by epithelial thickening can occur to "fill in" concave corneal surface irregularities; conversely, post-Tx epithelial remodeling by epithelial thinning can occur over convex corneal surface irregularities. In some embodiments, PV Tx areas, PV HAZs, PV Tx geometrical arrangements and PV Tx conditions are configured to produce smoother, lower corneal curvature gradients than produced by previous devices and methods. Corneal topography measurements can be used to measure corneal curvature gradients and smoothness.

In some embodiments, the present invention includes a time coordinate (t) that can be referenced to the photoirradiation start time. In some embodiments, photovitrification (PV) treatment (Tx) includes at least one of the following: (A) photoirradiance distributions within the two spatial coordinates (r,θ) of each PV Tx area on the anterior cornea, (B) the overall PV Tx geometrical arrangement of PV Tx areas, (C) three spatial coordinates (r,θ,z) of each PV Tx heat affected zone (HAZ), including densified corneal stromal tissue volume, (D) the photoirradiation time-dependent waveform (e.g., photoirradiance vs. time), (E) the thermal history distributions within PV HAZs, (F) the external stress applied onto each PV Tx area by a reverse template (RT), and/or (G) phenomenology (e.g., rates and mechanisms) of corneal stromal changes produced by thermal history distributions within PV HAZs associated with increasing beneficial effects for modification of corneal structure and properties, including but not limited to corneal optical aberrations, corneal elastic modulus or for any combination thereof while decreasing undesirable effects such as collateral damage to the cornea, including but not limited to the anterior basement membrane (BM) and to keratocytes (Ks). In some embodiments of the present invention, PV Tx conditions leave Ks maximally quiescent, while minimizing formation and activity of the fibroblast phenotype.

In some embodiments, the thermal history distributions within photovitrification (PV) heat affected zones (HAZs)—item E above—are influenced by at least one of the following: (A) photoirradiance distributions within the two spatial coordinates (r,θ) of each PV treatment (Tx) area on the anterior cornea, (B) the overall PV Tx geometrical arrangement of PV Tx areas, (C) three spatial coordinates (r,θ,z) of each PV HAZ, including densified corneal stromal tissue volume, and (D) the photoirradiation time-dependent waveform (e.g., photoirradiance vs. time). In some embodiments, the thermal history distributions within PV HAZs are also influenced by at least one of the following: (H) photoirradiation wavelength(s) (for which the corneal epithelium and corneal stroma have temperature-dependent absorption coefficients) and (I) thermal diffusion (TD) of three types: (I1) TD within the PV Tx areas of the cornea and the PV HAZs, (I2) TD from the PV Tx areas and PV HAZs both radially and axially into surrounding tissue, and (I3) TD axially from the cornea into the optical element of the ocular fixation device.

In some embodiments, specific photoirradiation wavelength(s) produce increased targeting of anterior corneal stroma with simultaneous minimization of deleterious effects on corneal tissue that is not intended to be part of the photovitrification (PV) heat affected zone (HAZ) that produces modification of corneal structure and properties, including but not limited to corneal elastic modulus, corneal optical aberrations, or any combination thereof.

In some embodiments, improvement of modification of corneal structure and properties, including corneal elastic modulus, corneal optical aberrations, or any combination thereof effects is associated with (A) photoirradiance distributions within the two spatial coordinates (r,θ) of each photovitrification (PV) treatment (Tx) area on the anterior cornea and (C) three spatial coordinates (r,θ,z) of each PV HAZ, as noted above. In some embodiments, the use of the reverse template to enhance vitrification modifications each PV treated volume produces an increased corneal stromal densification, resulting in increased magnitude of, and duration of, modification of corneal structure and properties, including but not limited to corneal elastic modulus, corneal optical aberrations, or any combination thereof effects.

Figure 12A:
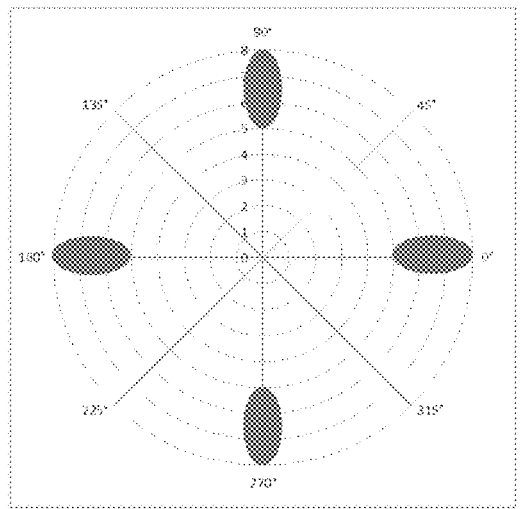
FIGS. 12A through 12D: Examples of photovitrification treatment (Tx) geometrical arrangements of Tx areas. Concentric circles are on millimeter intervals and are centered with respect to the pupil centroid (or another centration reference).
Figure 12B:
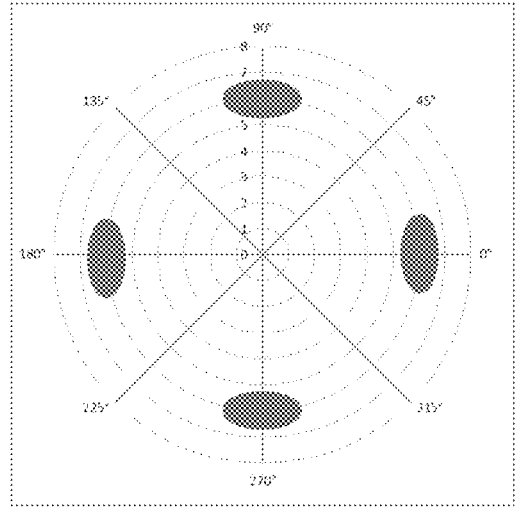
Figure 12C:
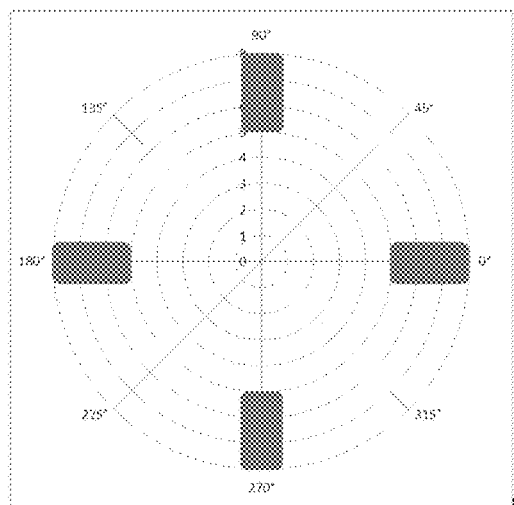
Figure 12D:
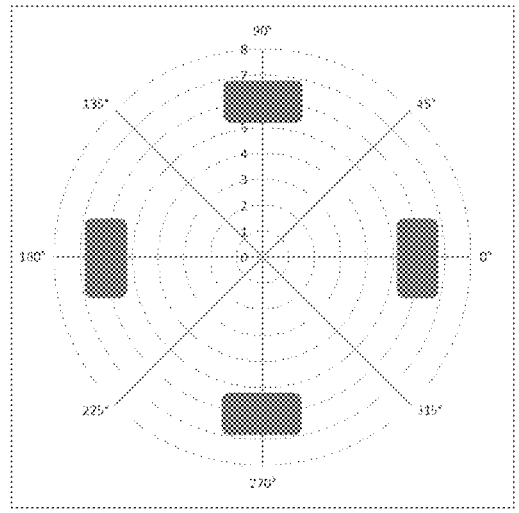

In some embodiments, FIGS. 12A through 12D show examples of photovitrification (PV) treatment (Tx) geometrical arrangements with PV Tx area locations and orientations that can be used for modification of corneal structure and properties, including but not limited to corneal optical aberrations, corneal elastic modulus or for any combination thereof. All of the PV Tx areas in FIGS. 12A through 12D examples are continuous PV Tx areas on four semimeridians, rather than discontinuous sets of PV Tx areas on each semimeridian. FIGS. 12A and 12B show elliptical PV Tx areas with long axes aligned on semimeridians (12A) or long axes aligned perpendicular to semimeridians (12B). FIGS. 12C and 12D show rectangular PV Tx areas aligned along (12C) or perpendicular to (12D) 0°, 90°, 180°, and 270° semimeridians. In some embodiments, continuous PV Tx areas and the PV Tx geometrical arrangements shown in FIGS. 12A through 12D are used for modification of corneal structure and properties, including but not limited to corneal optical aberrations, corneal elastic modulus or for any combination thereof.

Figure 13:
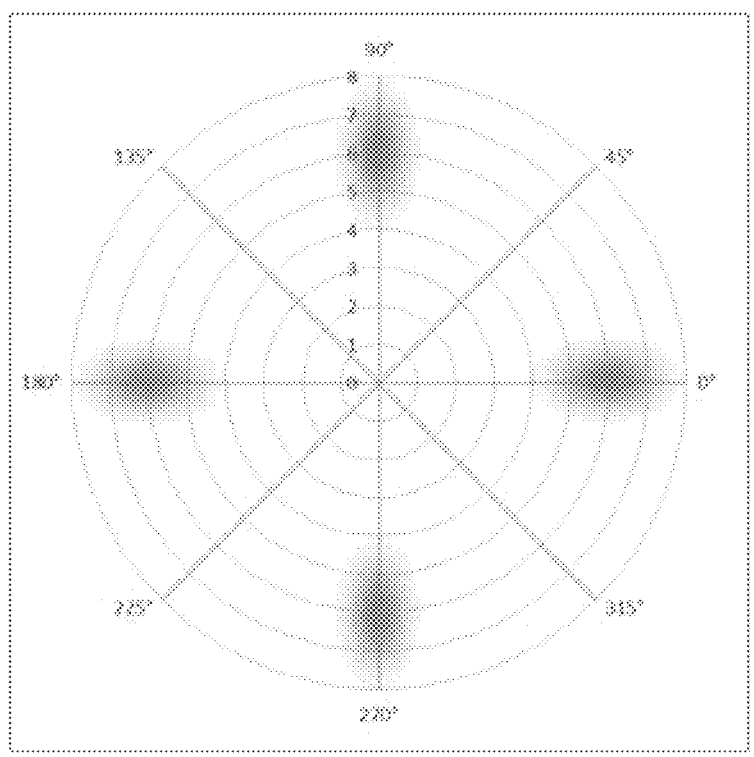
FIG. 13: Example photovitrification treatment geometrical arrangement of Tx areas. Concentric circles are on millimeter intervals.

FIG. 13 shows an additional example of a photovitrification (PV) treatment (Tx) geometrical arrangement with PV Tx area locations and orientations that can be used for modification of corneal structure and properties, including but not limited to corneal optical aberrations, corneal elastic modulus or for any combination thereof. All of the PV Tx areas in the FIG. 13 example are continuous elliptical PV Tx areas with PV Tx distributions peaked in the centers of PV Tx areas and then decreasing gradually as a function of distance from the center, in order to provide smooth gradients of corneal curvature change in the PV Tx areas. In some embodiments, PV Tx areas, with large diameters and smooth, gradual corneal curvature changes, and the PV Tx geometrical arrangement shown in FIG. 13 are used for modification of corneal structure and properties, including but not limited to corneal optical aberrations, corneal elastic modulus or for any combination thereof.

In some embodiments, gradients of corneal curvature changes (and, therefore, gradients of refraction changes) together with corneal surface roughness, are reduced to decrease epithelial modification. In some embodiments, angular segments (also referred to as "angular sectors") are "blended" into each other using gradients of refractive change that provide "transition zones". For example, FIGS. 13A and 13B show the difference between "step functions" of refractive change (FIG. 13A) and the present specification of "blended" gradients of refractive changes within "transition zones" (FIG. 13B). In an embodiment, FIG. 13B illustrates refractive change (D: Diopters) vs. semimeridian for four-fold photovitrification (PV) treatment (Tx) geometrical arrangements. In some embodiments, corneal curvature gradients between and within at least one of the following: angular segments, radial segments, or any combination thereof are in the range of 0.1 to 3 diopters (D) per millimeter.

In some embodiments, "step functions" of refractive change, as shown in FIG. 13A, are actually a multiple "bifocal" design with maxima at 90°, 180°, 270° and 360° (360° is the same as 0°) having 3 Diopters (D) more refraction than the minima at 45°, 135°, 225° and 315°; the maxima have more refraction to provide functional near vision while the minima have no additional refraction and are used for functional distance vision by emmetropic patients with age-related focus dysfunction. In an embodiment, the 3 D range of refraction change is shown in FIG. 13A and FIG. 13B. In some embodiments, for eyes with low myopia, the range of refraction change can be reduced. In some embodiments, the range of refraction change is increased. In some embodiments, the multiple "step function" design is the similar to the discontinuous refraction design used in bifocal intraocular lenses, spectacles and/or contact lenses. In some embodiments, a trifocal design is used to provide functional intermediate distance vision (in addition to near and far vision). In some embodiments, the multiple "sigmoid function" design, as shown in FIG. 13B, is a multifocal design with considerable "weighting" near maxima and minima semimeridians but with additional multifocality over the full range of refractive additions ("adds") including those used for functional intermediate vision. In some embodiments, the multiple "sigmoid function" design is similar to the refractive variation used in progressive lens spectacles and contact lenses and provides functional intermediate distance vision. In some embodiments, other oscillatory functions such as a sine function can be used.

Figure 14A:
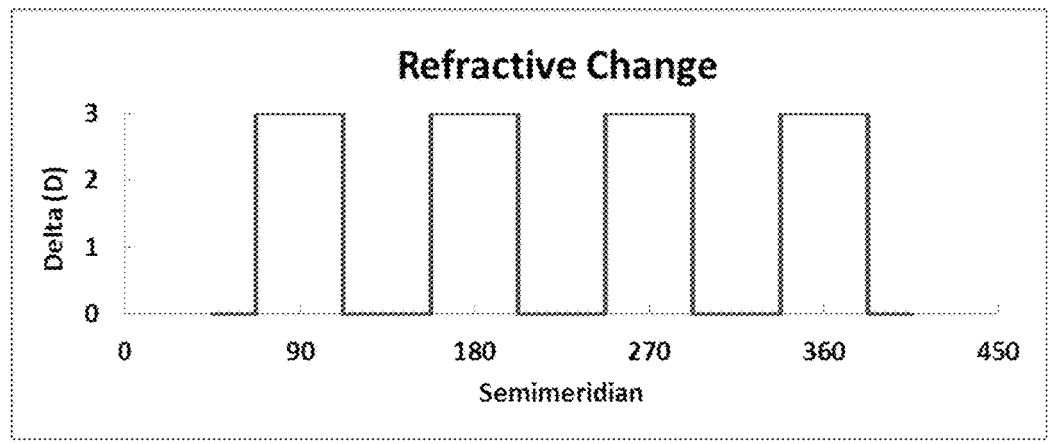
FIGS. 14A (top) and 14B (bottom): Refractive change (D: Diopters) vs. semimeridian for treatment (Tx) geometrical arrangements with four Tx areas. Top: step functions. Bottom: sigmoid functions.
Figure 14B:
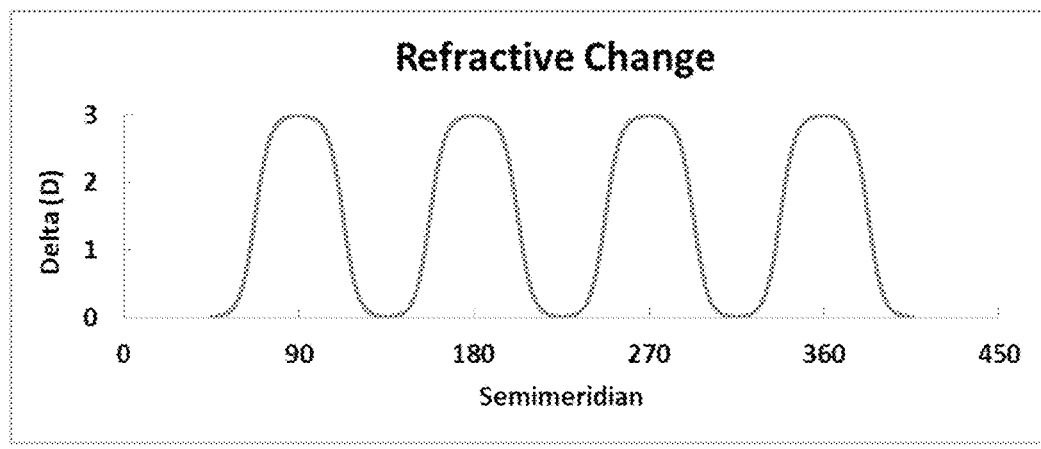
Figure 15A:
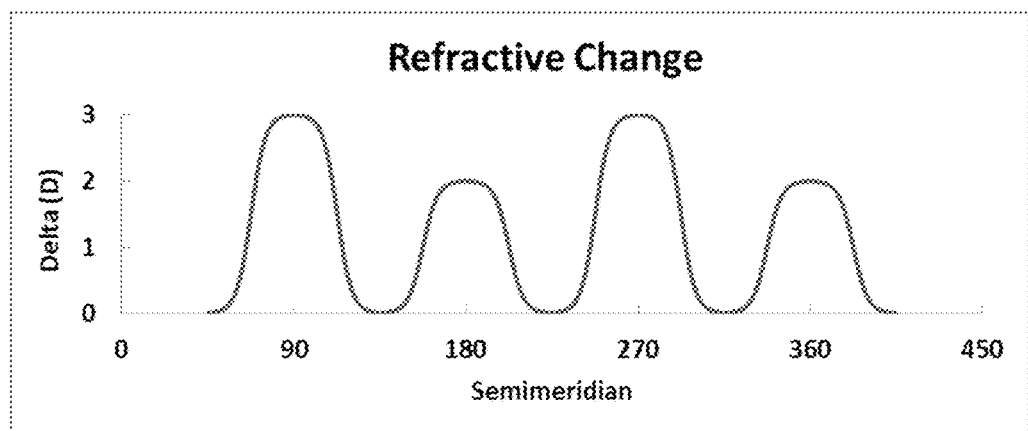
FIGS. 15A (top) and 15B (bottom): Refractive change (D: Diopters) vs. semimeridian for treatment (Tx) geometrical arrangements with four Tx areas. Top: Tx geometrical arrangement for reduction of regular astigmatism. Bottom: Tx geometrical arrangement including compensation for epithelial thickness variation.
Figure 15B:
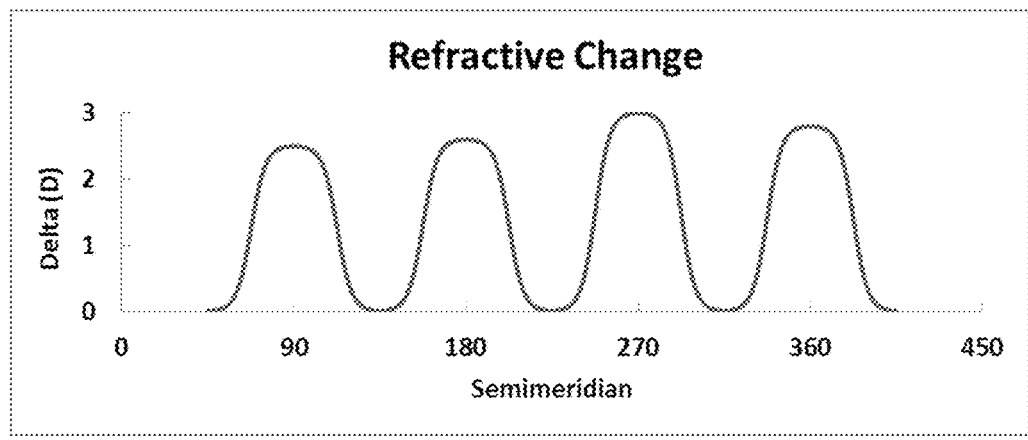

Other geometrical arrangements of "blended" gradients of refractive change within "transition zones" can be used to at least reduce symptoms associated with astigmatism and/or to adjust photovitrification (PV) treatments (Txs) to compensate for naturally occurring and iatrogenic epithelial thickness variations. FIGS. 14A and 14B show example PV Tx geometrical arrangements that can be used to at least reduce regular astigmatism (14A) and to provide unequal treatment energy densities to compensate for epithelial thickness variations (14B). In some embodiments, FIG. 14A and 14B illustrate refractive change (D: Diopters) vs. semimeridian for four-fold PV Tx geometrical arrangements that are used for two applications: FIG. 14A shows a regular astigmatism-affecting (i.e., at least regular astigmatism-reducing) PV Tx energy density geometrical arrangement and FIG. 14B shows an unequal PV Tx energy density geometrical arrangement to compensate for epithelial thickness variation.

In some embodiments, in the regular astigmatism photovitrification (PV) treatment (Tx) example (FIG. 14A), the PV Tx energy density is intended to produce a 3 Diopter (D) change at 90° and 270° but only a 2 D change at 180° and 360°. This regular astigmatism PV Tx geometrical arrangement is useful both to alleviate/lessen the symptoms of 1 D of pre-Tx regular astigmatism (with the flatter meridian along the 90°/270° axis) and to provide simultaneous functional distance, intermediate and near visual acuity. In some embodiments, the regular astigmatism PV Tx geometrical arrangement may have only two maxima and two minima, rather than the four-fold PV Tx geometrical arrangement shown in FIG. 14A.

In some embodiments, FIG. 14B illustrates compensation for naturally occurring and iatrogenic epithelial thickness variation; a purely spherical photovitrification (PV) treatment (Tx) is intended, but unequal PV Tx energy densities are used, with intended amounts to produce between 2.5 to 3.0 D of refractive change in the absence of epithelial thickness variations. Corneal epithelial thicknesses vary from eye to eye and from region to region on each eye. In some embodiments, on average, the superior (e.g., 90°) corneal epithelium is thinnest and the inferior (e.g., 270°) corneal epithelium is thickest. On average, the nasal and temporal corneal locations (180° and 360° in the left eye—OS, respectively; reversed in the right eye—OD) have intermediate epithelial thicknesses. The epithelium absorbs laser energy, but does not contribute to corneal stromal vitrification. Corneal epithelial thickness variations cause unequal changes in dosimetry—i.e., the "dose" of photons to the corneal stroma. In some embodiments, the PV Tx energy density is adjusted to compensate for epithelial thickness effects on dosimetry in each PV Tx area; epithelial thickness variations can be measured by optical coherence tomography and high frequency ultrasound biomicroscopy. In some embodiments, the requirement for PV Tx energy density adjustment can be modified by using external stress with the reverse template. In some embodiments, the reverse template can comprise at least one projection from the optical element of the ocular fixation device in contact with the anterior corneal surface and contacting the PV Tx areas; said projection(s) have a thickness in the range of 10 to 100 μm.

In some embodiments, gradual corneal curvature gradient changes and gradual refraction changes, together with reduced corneal surface roughness, reduce post-Tx epithelial modification that results in regression of modification of corneal structure and properties, including but not limited to corneal optical aberrations, or any combination thereof effects. Typically, after refractive surgery, epithelial modification occurs to reduce corneal surface irregularities and thereby to restore a smooth anterior corneal surface; this post-Tx epithelial modification is a major contribution to regression of modification of corneal structure and properties, including corneal optical aberrations, or of any combination thereof effects. The "step function" change in refraction shown in FIG. 13A promotes extensive and rapid epithelial modification in order to "smooth over" the irregular surface. In some embodiments, the "sigmoid" function change in refraction shown in FIG. 13B reduces epithelial modification and regression of modification of corneal structure and properties, including corneal optical aberrations, or of any combination thereof.

In some embodiments, surface root-mean-square (RMS) roughness in each PV Tx area is reduced to 10 μm or less. In some embodiments, corneal surface curvature gradients are reduced to 3 diopters (D) per millimeter (mm) or less (≤3 D/mm).

In some embodiments, smoother refractive changes (and hence smoother and lower magnitude corneal surface curvature gradients) associated with the sigmoid functions shown in FIGS. 13B, 14A and 14B can produce less, and slower, epithelial modifications compared to the "step function" example in FIG. 13A. In some embodiments, the detailed refractive changes (in terms of the sector widths of maxima and minima of the sigmoid functions, together with corneal curvature gradients) can be adjusted by specification of photovitrification (PV) treatment (Tx) areas, PV heat affected zones (HAZs), PV Tx geometrical arrangements and PV Tx conditions. In some embodiments, the detailed refractive changes can be adjusted to optimize corneal optical aberration modification effects. In some embodiments, as a design objective, configuration of the complete shapes (lengths, widths, and depths), thermal histories and PV Tx geometrical arrangements of PV HAZs maximize targeted beneficial effects including, but not limited to, modifications of corneal stromal structure and properties, including but not limited to corneal optical aberrations, corneal elastic modulus or any combination thereof and minimize deleterious effects including, but not limited to, damage to corneal structures, regression of modification of corneal structure and properties, including corneal optical aberrations, or any combination thereof.

In an embodiment, an example of photovitrification (PV) treatment (Tx) area dimensions is shown schematically in FIG. 13 for a 4-fold PV Tx geometrical arrangement. In some embodiments, each PV Tx area is elliptical in shape and each PV heat affected zone (HAZ) has depth variation with the deepest portion in the center of each PV Tx area; the centers of the PV Tx areas are on the 90°, 180°, 270° and 360° semimeridians and therefore correspond to the maxima in FIG. 13B. In some embodiments, the PV HAZ depths (and the magnitudes of change in corneal optical aberrations and refractions) are graduated from the centers of the PV Tx areas and decrease as a function of distance from the center of each Tx area. In some embodiments, dimensions of PV Tx areas and PV HAZs, including full width at half maximum (FWHM) depth, can vary. In some embodiments, shapes of PV Tx areas can be selected from the group consisting or, but not limited to: circular, elliptical, oval, stadium, polygonal, polygonal with rounded corners, arcuate, annular, or any combination thereof. In some embodiments, varying numbers of PV HAZs with specified shapes and volumes (i.e., r,θ,z dimensions) in a specified PV Tx geometrical arrangement and photoirradiated using specified PV Tx conditions, with or without a reverse template to provide external stress during PV Tx, can also be used to optimize targeted beneficial effects including, but not limited to, modifications of corneal stromal structure and properties, including but not limited to corneal optical aberrations, and to minimize deleterious effects including, but not limited to, damage to corneal structures, regression of modification of corneal structure and properties, including but not limited to corneal elastic modulus and corneal optical aberrations, or any combination thereof In some embodiments, photovitrification (PV) treatments (Txs) produce localized PV heat affected zones (HAZs) but non-localized modification of corneal structure and properties, including but not limited to corneal elastic modulus and corneal optical aberrations, or any combination thereof due to the complex biomechanics of the cornea. In an embodiment, although the PV HAZs shown in FIG. 13 are located in the periphery of the cornea, modification of corneal structure and properties, including but not limited to corneal optical aberrations, corneal elastic modulus or any combination thereof can extend to the center of the cornea. In an embodiment, FIG. 13 shows a 4-fold PV Tx geometrical arrangement wherein concentric rings are at 1 mm diameter intervals and are centered with respect to the pupillary centroid (or with respect to another centration reference such as the coaxially sighted corneal light reflex). In an embodiment, FIG. 13 shows gradations of PV Tx areas and accompanying PV HAZs, with gradations schematically indicated by shading, i.e., the darker the shade, the deeper the PV HAZ and the larger the modification of corneal structure and properties.

In some embodiments, the present invention produces photovitrification (PV) heat affected zones (HAZs) in axisymmetric geometrical arrangements centered on the pupil centroid (or another centration reference) in order to minimize the occurrence of induced astigmatism. In some embodiments, PV treatment (Tx) energy density within each PV Tx area can be adjusted to compensate for epithelial thickness variations and thereby minimize the occurrence of induced astigmatism and/or reduce the symptoms of astigmatism. In some embodiments, polar coordinates r,θ of each PV Tx area are adjusted to compensate for epithelial thickness variations and for pre-Tx astigmatism.

In some embodiments, FIGS. 13, 14A, 14B, 15A and 15B are examples of symmetrical 4-fold Tx geometrical arrangements of corneal curvature (and, therefore, corneal refraction) changes. In some embodiments, Tx geometrical arrangements such as symmetrical 2-fold, 6-fold, 8-fold, 10-fold, and 12-fold Tx geometrical arrangements are utilized for modification of corneal structure and properties, including but not limited to corneal optical aberrations, corneal elastic modulus or for any combination thereof. In some embodiments, asymmetrical and/or odd number-fold (e.g., single Tx area and 3-fold and 5-fold Tx areas) Tx geometrical arrangements are utilized.

Figure 16:
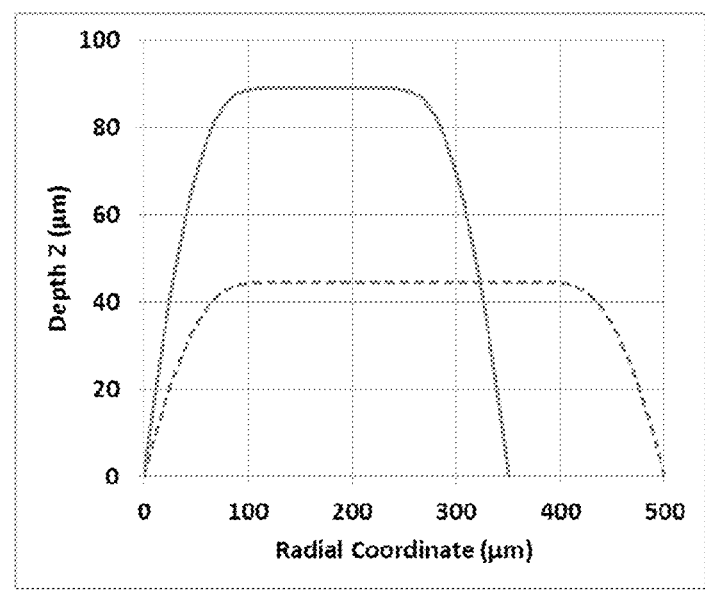
FIG. 16: Heat affected zone (HAZ) cross-sections: solid—HAZ1, dashed—HAZ2. In the figure, note that the radial coordinate is compressed relative to the depth coordinate.

In some embodiments, the present invention utilizes various sizes of photovitrification (PV) heat affected zones (HAZs). In an embodiment, FIG. 16 shows cross-sections through two PV HAZs that are solids of revolution having approximately equal volumes: wherein the solid line is a "deeper" PV HAZ1 that has a base [at z=0 μm in the corneal stroma (S)] ca. 350 μm in diameter and that extends to a depth z=ca. 90 μm and wherein the dashed line is a "shallower" PV HAZ2 that has a base (at z=0 μm in the S) ca. 500 μm in diameter and that extends to a depth z=ca. 45 μm. FIG. 16 shows a solid line that is a cross-section associated with PV HAZ1 and a dashed line that is a cross-section associated with PV HAZ2. In FIG. 16, the radial coordinate is compressed relative to the depth coordinate. In an embodiment, FIG. 16 shows the dimensions of PV HAZ2 adjusted so that it has twice the PV Tx area (at z=0 μm) of PV HAZ1 and nearly equal volume as PV HAZ1. In some embodiments, the inventive system(s) can include(s) a quasi-cw photon output, wherein the quasi-cw photon output can include a single and/or multiple pulse(s) of energy, wherein each pulse can be constant in instantaneous power or can be non-constant, with time-dependent waveform modifications that change instantaneous power.

In some embodiments, the photovitrification (PV) heat affected zone (HAZ) area is increased, PV HAZ depth is reduced, and the corneal curvature gradient is decreased while conserving the acute modification of corneal structure and properties, including but not limited to corneal optical aberrations, corneal elastic modulus or any combination thereof effect. In some embodiments, these changes reduce epithelial modification and exhibit increased efficiency since reducing the depth of anterior stroma targets the more interwoven collagen lamellae (See FIG. 4) that have greater biomechanical effect in producing modifications including but not limited to modifications of corneal optical aberrations, corneal elastic modulus, or any combination thereof.

In some embodiments, the photovitrification (PV) heat affected zone (HAZ) is increased in area by increasing the area of the photoirradiated cornea. In some embodiments, one device for increasing the area is an adjustable spacer between the optical fiber tips (and/or between any optical elements that are used to modify the photon distribution emerging from the optical fiber tips) and the thermally conductive optical element of the optical fixation device in contact with the cornea. In some embodiments, spacings of optical delivery elements with respect to the optical fixation device's optical element are adjusted automatically as specified by a treatment nomogram to obtain a predetermined magnitude of corneal optical aberration change and/or to specialize treatment for a particular indication for use (IFU).

In some embodiments, outputs from optical fibers can be modified by additional optics including, but not limited to: cylindrical lenses, Powell lenses (one type of aspheric lens), axicons or any combination thereof, to produce specified photovitrification (PV) treatment (Tx) areal shapes. In some embodiments, Powell lenses are manufactured with different "fan angles" to produce different "line" lengths. In some embodiments, "line" lengths are increased by increasing the spacing between the flat (exit) face of the lens from the substrate. In some embodiments, custom Powell microlenses are manufactured using a transparent material (e.g., low OH silica) and these lenses are mounted in an assembly that spaces the lenses in apposition with optical fibers to produce a Tx geometrical arrangement. In some embodiments, the cylindrical lens yields a non-uniform (Gaussian) irradiance distribution while the Powell lens yields a uniform irradiance distribution within the line (rectangle) segment.

In some embodiments, the Powell lens photovitrification (PV) treatment (Tx) area improves the radial distribution of Tx effect. In some embodiments, the PV Tx area has a graduated angular distribution for PV Tx effect (e.g., as shown in FIGS. 13B, 14A and 14B). In some embodiments, each PV Tx area can be configured to have a larger area (e.g., length and width) so that there is reduced discontinuity, with shallower depth and reduced depression and with smoother corneal curvature gradient.

In some embodiments, at least one photon source can be used to produce photons for photovitrification (PV) Txs. In some embodiments, at least one photon source and associated optical fiber delivery subsystem can produce improved PV Tx geometrical arrangements with graduated (e.g., smooth corneal curvature gradient) radial and angular light distributions. In some embodiments, the inventive devices of the present invention can utilize at least one photon source wherein its output beam is then split into two or more "beamlets" wherein each "beamlet" is independently controlled. As an example, a continuous wave (cw) solid state laser comprising a host material doped with at least one lasing material can produce a collimated, low divergence beam. A sample description follows: (A) a laser beam is directed into a beam distribution system, and/or (B) the beam distribution system includes a shutter for providing a configured exposure duration of the laser light, a beamsplitting optical system comprising one or more beamsplitters to produce beamlets, beamlet steering and focusing optics to direct focused beamlet light into optical fibers, a translation stage to move optical fiber arrays into position to receive focused beamlet light, a position controller to position the translation stage and (C) beamlet attenuators and/or beamlet modifiers to adjust the amount of focused beamlet light directed into optical fibers; these beamlet attenuators and/or modifiers can be independently controlled to adjust the amount of predetermined beamlet light directed into individual optical fibers.

In some embodiments, multiple photon sources including but not limited to lasers, intense pulsed light sources, or any combination thereof are used to maximize targeting of beneficial corneal stromal modifications as well as to minimize deleterious effects such as damage to corneal structures. In some embodiments, all of the multiple photon sources have substantially the same output characteristics including, but not limited to: wavelength(s), time-dependent waveform(s) and instantaneous power(s). In some embodiments, at least one of the multiple photon sources has different wavelength(s) from at least one other photon source. In some embodiments, at least one of the multiple photon sources has different time-dependent waveform(s) from at least one other photon source. In some embodiments, at least one of the multiple photon sources has different instantaneous power(s) from at least one other photon source.

In some embodiments, the corneal curvature gradient can be reduced by changing the photoirradiation distribution so that the photovitrification (PV) heat affected zone (HAZ) is increased in area and is shaped, in part, by external pressure on the PV HAZ by a reverse template.

In some embodiments, the photovitrification (PV) heat affected zone (HAZ) depth can be decreased by increasing the absorption coefficient and/or by changing the laser irradiation waveform to a shorter duration of irradiation time. In some embodiments, a more complicated photoirradiation waveform is used by "ramping up" the photoirradiance and/or by using multiple photoirradiation times. In some embodiments, more complicated photoirradiation waveforms increase the amount of PV Tx within the PV HAZ while preventing collateral damage. In some embodiments, multiple laser wavelengths can be used within each Tx area in order to enlarge the axial extent of the HAZ and to make the thermal history of treated corneal stromal tissue in the axial coordinate more uniform. In some embodiments, the thermal history within the radial coordinate of each Tx area can be made more uniform by using an irradiance distribution including, but not limited to, a "flat top" distribution, a superGaussian distribution, a "doughnut" distribution or any combination thereof. In some embodiments, the PV HAZ depth can also be modified by the amount of external stress and resulting external pressure applied using a reverse template.

In some embodiments, rotation of the photovitrification (PV) treatment (Tx) geometrical arrangement so that the PV Tx areas are centered on predetermined semimeridians can be automated by several means such as by using electromechanical actuators or a miniature Dove prism to rotate the optical fiber array around the z-axis (See FIG. 2).

In some embodiments, the overall photovitrification (PV) treatment (Tx) geometrical arrangement can be changed by using different optical fiber arrays and/or by adjusting optical fibers within an array. In some embodiments, the PV Tx geometrical arrangement can be altered by automatically changing the centerline diameters of rings of PV Tx areas using electromechanical actuators as specified by a Tx nomogram in order to obtain a predetermined magnitude of corneal optical aberration change or predetermined magnitude of cornea properties change and/or to specialize PV Tx for a particular Indication For Use.

In some embodiments, the range of corneal curvature change includes, but is not limited to, corneal curvature change between 0.1 to 20 diopters (D). In some embodiments, the range of corneal curvature gradient includes, but is not limited to, corneal curvature gradient between 0.1 D/mm to 3 D/mm. In some embodiments, the range of photovitrification (PV) treatment (Tx) area includes, but is not limited to, PV Tx area between 0.2 mm$^2$ to 100 mm$^2$. In some embodiments, corneal vitrification, including but not limited to photovitrification, can be used to change corneal curvature for a range of, including but not limited to, 0.1 to 20 diopters. In some embodiments, corneal vitrification, including but not limited to photovitrification can be used to stabilize or decrease or any combination thereof of naturally occurring corneal ectasia; iatrogenic corneal ectasia; or any combination thereof; wherein the decrease in corneal ectasia includes at least one local change to corneal curvature within at least one local area bounded by r,θ coordinates wherein the change to corneal curvature is between 0.10 diopters (D) and 20 D.

In some embodiments, the present invention includes: A—corneal vitrification, including but not limited to photovitrification (PV) treatment (Tx), changes affecting lower order aberrations (LOAs) including tip, tilt, defocus and astigmatism; B—PV Tx changes affecting higher order aberrations (HOAs) including, but not limited to, spherical aberration, coma, trefoil, and/or higher order astigmatism; C—PV Tx changes affecting aberrations that are not described predominantly (at least 51%) by Zernike polynomials (and their coefficients) up to and including 8$^{th}$ radial order; and D—any combination thereof in order to produce modification of corneal optical aberrations to affect (e.g., optimize) functional simultaneous vision at all distances (near, intermediate and far) and to affect (e.g., improve) quality of vision (with respect to quality measures including, but not limited to, contrast sensitivity and stereoacuity). In some embodiments, defocus is the LOA that is modified to affect (e.g., correct) or at least reduce spherical refractive errors of myopia and hyperopia, to magnify the retinal image, or to provide any combination thereof. In some embodiments, astigmatisms—both vertical and horizontal— are the LOAs that are modified to affect (e.g., correct) or at least reduce regular astigmatism. In some embodiments, HOAs (for example, spherical aberration—both primary and secondary, coma and trefoil) are optimized in order to provide vision improvement (for example, increased depth of field) to compensate, at least in part, for age-relayed focus dysfunction; other HOAs can also be represented by terms in the Zernike basis set to include, for example, the graduated refractive changes discussed in connection with FIGS. 14B, 15A, and 15B. In some embodiments, LOAs, HOAs (in general, all of the HOAs represented by terms in the Zernike polynomial basis set) and other aberrations that are not described predominantly (at least 51%) by Zernike polynomials (and their coefficients) up to and including 8$^{th}$ radial order are modified in a complex manner in order to eliminate or at least reduce vision defects due to irregular corneal disorders including, but not limited to, keratoconus, naturally occurring ectasias and iatrogenic ectasias. In some embodiments, one or more LOAs and HOAs are modified to relocate images on the retina. In some embodiments, the inventive devices and methods of the present invention are utilized to modify LOAs. In some embodiments, the inventive devices and methods of the present invention are utilized to modify the LOA of defocus. In some embodiments, the inventive devices and methods of the present invention are utilized to modify the LOAs of vertical and horizontal astigmatism (cylinder). In some embodiments, the inventive devices and methods of the present invention are customized to simultaneously modify the LOAs of defocus and vertical and horizontal astigmatism. In some embodiments, the inventive devices and methods of the present invention are customized to modify one or more HOAs (e.g., coma, trefoil, spherical aberration—both primary and secondary, and other HOAs) or any combination thereof.

In some embodiments, the inventive devices and methods of the present invention are customized to modify one or more aberrations that are not described predominantly (at least 51%) by Zernike polynomials (and their coefficients) up to and including 8$^{th}$ radial order.

In some embodiments, a simultaneous vision simulator using adaptive optics can be used to "personalize" photovitrification (PV) treatment (Tx) for each eye to obtain improved binocular visual acuity for objects at all distances (near, intermediate and far) and for all illumination conditions (photopic, mesopic, and/or scotopic) and to obtain an improved quality of vision with respect to other considerations including, but not limited to: contrast sensitivity, stereoacuity, freedom from optical dysphotopsias, modulation transfer function, point spread function, and Strehl ratio. In some embodiments, PV Tx geometrical arrangements can be adjusted to modify and/or customize and/or personalize patient PV Txs to affect (e.g., optimize) a combination of LOAs, HOAs and other aberrations that are not described predominantly (at least 51%) by Zernike polynomials (and their coefficients) up to and including 8$^{th}$ radial order. In some embodiments, the changes of LOAs, HOAs and other aberrations that are not described predominantly (at least 51%) by Zernike polynomials (and their coefficients) up to and including 8$^{th}$ radial order are accomplished with the device of this invention by photoirradiating an asymmetric PV Tx geometrical arrangement wherein: A—PV Tx areas are in an axisymmetric PV Tx geometrical arrangement of an even number of PV Tx areas that are photoirradiated with different PV Tx energies [in addition to those differences in PV Tx energies used for reducing regular astigmatism and for compensating for naturally occurring and iatrogenic epithelial thickness variations], B—PV Tx areas are in an asymmetric PV Tx geometrical arrangement (either with an odd number of PV Tx areas or with an asymmetric PV Tx geometrical arrangement of an even number of PV Tx areas), or any combination thereof.

In some embodiments, a reverse template can be used to provide external stress to apply pressure to at least one treatment (Tx) area during photovitrification (PV) Tx. It is understood to those skilled in the art that the instant invention differs from orthokeratology (also termed orthokeratoplasty or corneal refractive therapy) and related procedures such as enzymatic orthokeratology, which involve corneal epithelial profile modification, and not the production of vitrified stromal issue, to modify optical aberrations. Orthokeratology involves and requires nightly wearing of a contact lens with the resulting temporary effects on optical aberrations dissipating during the day after contact lens wear at night. In contrast, in some embodiments, the instant invention produces corneal stromal modifications that include vitrified corneal stromal tissue with modification of structure and properties including increased corneal elastic modulus and enhanced stromal densification with external stress application with a reverse template during corneal photovitrification. In addition, in some embodiments, the instant invention can reduce progressive myopia, progressive axial elongation, or any combination thereof without ongoing treatment every night, unlike orthokeratology, because the instant invention provides effects lasting over years and not less than a day and, unlike orthokeratology, is without clinically significant side effects or complications such as corneal infections and scarring in the visual axis. In some embodiments, corneal vitrification, including but not limited photovitrification, can reduce progressive myopia, progressive axial elongation, or any combination thereof, wherein either or both progressions are reduced by at least 30% compared with those wearing conventional eyeglasses or single-vision soft contact lenses.

In some embodiments, corneal vitrification, including but not limited to photovitrification can provide vision improvement and can provide compensation, at least in part, for age related focus dysfunction wherein the vision improvement includes, but is not limited to, providing functional simultaneous vision at multiple viewing distances including, but not limited to, a near distance (ca. 40 cm), an intermediate distance (ca. 60 to 100 cm) and a far distance (300 cm or farther) and an increased depth of field wherein functional vision is 20/40 or better in Snellen terms (equivalent to 0.3 log MAR or less) and wherein depth of field includes the range of distance for which vision is functional. In some embodiments, vision improvement can be provided by increasing the quality of vision (QoV), including but not limited to, QoV measures of depth of field, contrast sensitivity, stereoacuity, modulus transfer function, point spread function and Strehl ratio.

In some embodiments, corneal vitrification, including but not limited to photovitrification, can be used to provide vision improvement and to overcome disorders causing central visual field deficits, including but not limited to retinal disorders such as age-related macular degeneration, by using modifications of corneal optical aberrations for image magnification on the retina, image relocation on the retina, or any combination thereof; wherein the image magnification provides a retinal image that overlaps functional regions of the retina and wherein the image relocation on the retina is to at least one preferred retinal location that overlaps functional regions of the retina.

Figure 17:
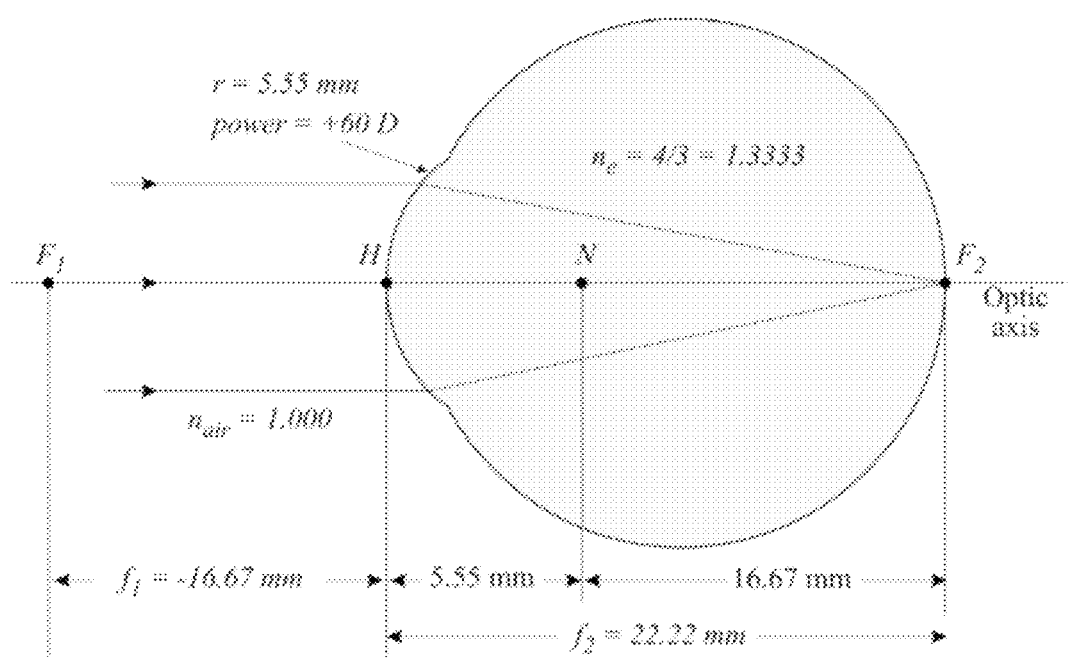
FIG. 17: Emsley schematic eye.

In some embodiments, image magnification on the retina can be produced by using corneal vitrification to modify optical aberrations including, but not limited to, defocus and spherical aberration. An estimate of the image magnification produced by corneal vitrification for modification of defocus can be calculated using the Emsley standard reduced 60-diopter (60 D) eye (the Emsley simplified eye) shown in FIG. 17—This simplified eye has a single refracting surface (at the cornea) and has one refractive power mismatch (at the cornea) with an assumed ocular index of refraction n'=1.3333; the air index of refraction is 1.00. For this simplified eye, +60 D refractive power corresponds to a radius of curvature r=5.55 mm for the single refracting surface. The focal points $F_1$ and $F_2$ are at −16.67 mm and +22.22 mm, respectively.

For an emmetrope with uncorrected distance visual acuity (UDVA)=20/20 (0.0 log MAR) and for the Emsley simplified eye with +60 D refractive power, the retinal image at $F_2$ for an object at infinity is ca. 5 µm per minute of arc the object subtends. Therefore, 1 mm image size on the retina X is approximately equivalent to 200 min arc. If r is decreased or increased, corresponding to increased or decreased refractive power, respectively (hence, myopia or hyperopia, respectively), the retinal image size X is increased and can be estimated by the size of the geometrical aberration-free defocus blur disc Φ:

$$\Phi = 3.483\ \Delta L\ D_{mm} \quad \text{(Equation 3)}$$

wherein Φ is the defocus blur disc [units: min arc],
ΔL is the defocus [units: diopters] and
$D_{mm}$ is the pupil diameter [units: mm].
The retinal image size X (in µm units)=50. The potential UDVA (in decimal units)=25/X.

Figure 18A:
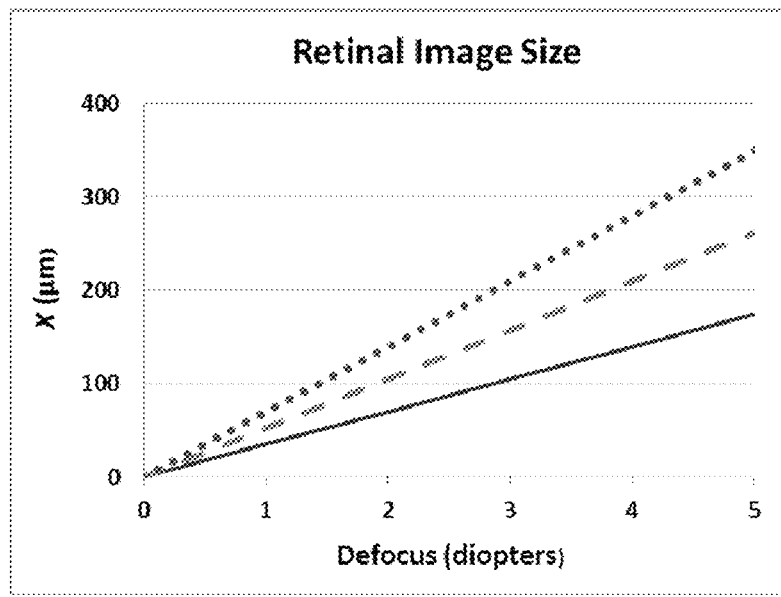
FIGS. 18A and 18B: Retinal Image Size X (top) and Potential UDVA (bottom) as functions of Defocus for three pupil diameters D.: 2 mm (solid line), 3 mm (dashed line) and 4 mm (dotted line).
Figure 18B:
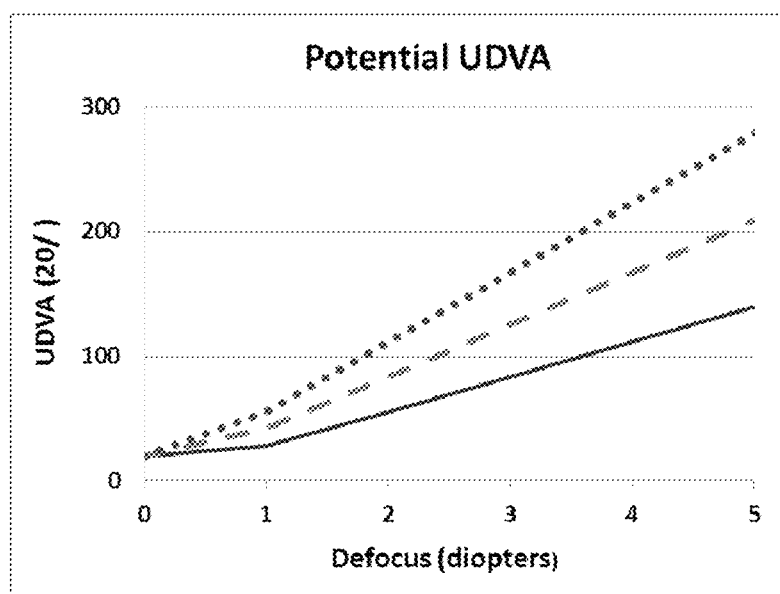

FIGS. 18A and 18B show calculated values, using Equation 3, of the retinal image size X and the potential UDVA (in Snellen units) for three pupil diameters $D_{mm}$ (2, 3 and 4 mm)—all for values of ΔL in the range of 1 to 5 D. The potential UDVA should be considered an upper limit to the actual value of UDVA since it represents an aberration-free (apart from defocus) value and also pertains to full function within the retinal image; some portion of the retinal image will be dysfunctional due to geographic atrophy or other factors.

In some embodiments, image relocation on the retina can be produced by corneal vitrification to modify optical aberrations including, but not limited to, tip, tilt and coma. In contrast to the image magnification case that involves modification of defocus and other optical aberrations such as spherical aberration that affect only the radial distribution of the image, modification of aberrations for image relocaion such as tip, tilt and coma affect the angular distribution of the image, thereby relocating its centroid (i.e., the average position of all the points in the image).

In some embodiments, corneal vitrification, including but not limited to photovitrification, can be used to stabilize or increase or any combination thereof at least one of: adhesion of apposed stromal tissue, including but not limited to after corneal wound closure; adhesion of donor transplanted corneal stromal tissue or synthetic implanted material to apposed host donor stromal tissue; or any combination thereof; wherein the increase in adhesion is 10% or greater.

In some embodiments, devices and methods of the inventions described herein are configured to target and maximize beneficial effects including, but not limited to, corneal vitrification, including, but not limited to, corneal photovitrification, corneal acoustic vitrification, or any combination thereof; modification of corneal structure and properties, including but not limited to corneal elastic modulus, corneal optical aberrations or any combination thereof; maximal maintenance of homeostatic activities of corneal stromal keratocytes with minimal transformation of keratocytes into fibroblasts and myofibroblasts; maximal maintenance of normal collagen fibrillar diameter; or any combination thereof, and are configured to minimize deleterious side effects including, but not limited to, damage to corneal structures, regression of modification of corneal structure and properties, including but not limited to corneal elastic modulus, corneal optical aberrations, or any combination thereof. In some embodiments, methods and systems for corneal vitrification, including but not limited to photovitrification, are configured not to prevent a wound healing response but, instead, primarily to reduce deleterious wound healing effects.

In some embodiments, the anterior corneal stroma is the principal corneal structure that is targeted in order to produce maximum beneficial effects. In some embodiments, deleterious effects including, but not limited to, deleterious alterations to the structure, function and properties of both the non-vitrified stroma and vitrified volumes are minimized Corneal stromal tissue vitrification in accordance with the present inventive methods and system(s) can involve modifications to in vivo corneal stromal tissue including, but not limited to:

A—modifications of stromal nano-, micro- and macrostructure, including but not limited to the fiber/matrix composite;

B—modifications of stromal fiber/matrix and cellular functions, including, but not limited to, metabolism, motility and interactions including signaling on all scales C—modification of stromal properties, including, but not limited to, mechanical, optical, thermal and transport properties) on all scales;

D—or any combination thereof.

Figure 19:
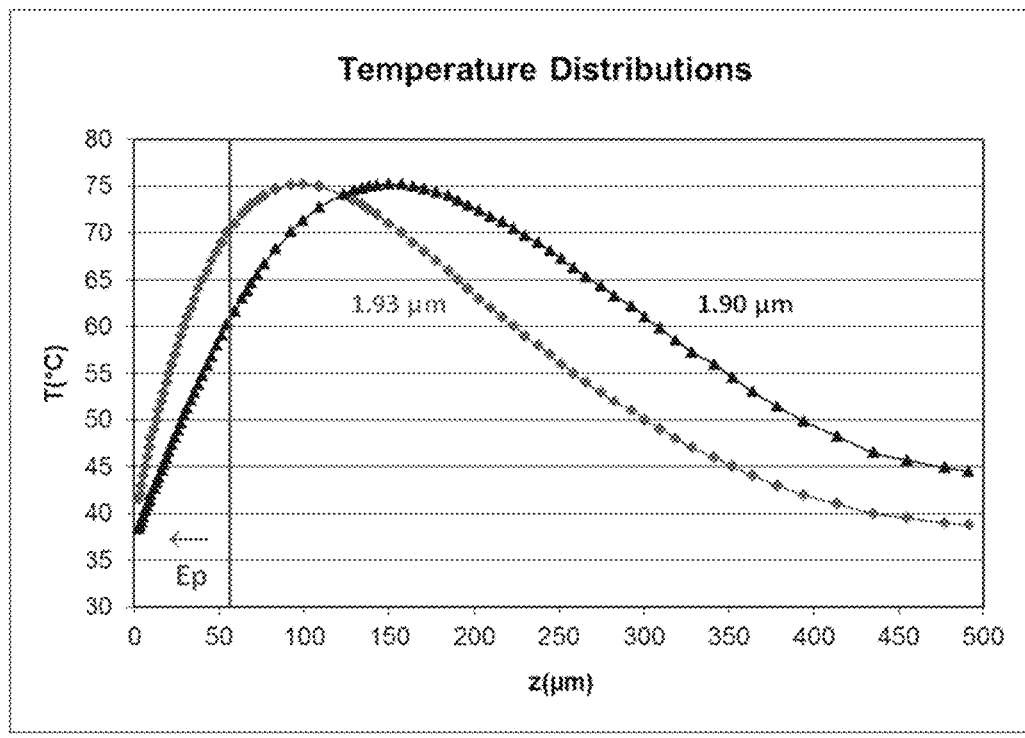
FIG. 19: Temperature distributions for matched treatment conditions except wavelength: 1.90 μm (triangles), 1.93 μm (diamonds). Epithelium (Ep) thickness is ca. 56 μm.

In some embodiments, the combination of a selected photon source wavelength together with an optical fixation device with a thermally conductive optical element can provide enhanced targeting and maximization of beneficial corneal stromal change, together with enhanced minimization of thermal damage to corneal structures. In some embodiments, photon source wavelengths in the range of 1.87 to 1.93 µm together with an optical fixation device with a thermally conductive optical element provide enhanced targeting and maximization of beneficial corneal stromal change, together with enhanced minimization of thermal damage to corneal structures wherein photon source wavelengths in the range of 1.87 to 1.93 µm make use of the temperature (T) dependence of the corneal absorption coefficient a in this wavelength range. As shown in FIGS. 7 and 8, water $\alpha$ (and hence cornea a since water is the predominant chromophore) increases by more than 30% as T increases from 22° to 70° C. In some embodiments, this T dependence can be used to advantage as shown in the example of FIG. 19 for photovitrification (PV) treatments (Txs) under matched Tx conditions except for photon source wavelength. Two T distributions are shown in FIG. 19, as calculated using a numerical finite element axisymmetric transient conduction heat transfer model to obtain two-dimensional (2-D) T distributions along the irradiation centerline (r=0). Calculations were completed using (A) 50 radial and 47 axial spatial node volumes with nonuniform spacing; (B) flat-top irradiation with a circular cross-section of 500 µm diameter and 50 W/cm² irradiance for 150 ms, (C) sapphire optical element (10 mm diameter, 1 mm thickness) in contact with the anterior corneal surface, (D) thermal properties: constant pressure heat capacity $C_p$=3.2 joule/(gram° C.), thermal conductivity K=2.9×10⁻³ watt/(cm° C.), thermal diffusivity $\kappa$=8.6×10-3 cm²/second; (E) different water absorption coefficients: at 1.93 µm, $\alpha$=125 cm⁻¹ and at 1.90 µm, $\alpha$=114 cm⁻¹ at 35° C. increasing linearly to $\alpha$=142 cm⁻¹ at 75° C. as shown in FIG. 8. In the absence of an optical fixation device with a thermally conductive optical element in contact with the corneal anterior surface and providing a temperature within ±5 degrees from a physiological cornea surface T (approximately at 35° C.) during photovitrification treatment, both of the T distributions for 1.90 µm and 1.93 µm photoirradiation would have T maxima in the corneal anterior membrane and basal epithelium at much higher T values than shown in FIG. 19, thereby destroying the corneal anterior membrane and basal epithelium. The optical fixation device with a thermally conductive optical element removes part of the heating produced by photoirradiation, yielding T maxima in the corneal stroma as shown in FIG. 19. In addition, the T dependence of the corneal absorption coefficient further differentiates effects of the two photoirradiations at different photon wavelengths. The T distributions for 1.90 µm and 1.93 µm PV Txs have the same peak T values of ca. 75° C. but the T distribution for 1.90 µm targets a larger volume of corneal stromal tissue over an extended temperature range (viz., 50 to 75° C.); in this case, 1.90 µm PV Tx yields a greater beneficial effect. The T distribution for 1.90 µm also provides greater minimization of heating and thermal damage to the anterior basement membrane and basal epithelium.

In some embodiments, corneal photovitrification can be optimized by time-dependent waveform modification of:
an individual photoirradiation pulse, or
a sequence of multiple photoirradiation pulses;
wherein the time-dependent waveform modification can be:
at least one time-dependent waveform modification of at least one pulse to change instantaneous power during the pulse waveform,
10 ms to 200 ms time-dependent spacings between multiple pulses;
or any combination thereof.

In some embodiments, several photovitrification (PV) treatment (Tx) parameters can be used to target and maximize beneficial effects and to minimize deleterious effects, wherein PV Tx parameters include, but are not limited to: wavelength, single pulse waveform (i.e., irradiance vs. time), multiple pulse waveform, Tx area, Tx geometrical arrangement, external stress by a reverse template, or any combination thereof. In some embodiments, ranges of PV Tx parameters that can be used to target and maximize beneficial effects and to minimize deleterious effects are listed in Table 1: Illustrative Ranges Of Treatment Parameters In Accordance With At Least Some Embodiments Of The Instant Invention; it is understood that PV Tx parameters can vary depending on the Indication for Use that is intended, so several ranges of PV Tx parameters are specified.

Table 2 provides words and/or terms in the context of at least some embodiments of the instant invention.

TABLE 1

Illustrative Ranges Of Treatment Parameters In Accordance With At Least Some Embodiments Of The Instant Invention..

| Treatment Parameter | Range |
| --- | --- |
| Vitrification within stromal vitrified volumes | 1% to 50% |
| Photon wavelength | All wavelengths at which water absorption coefficients are between 20 to 300 cm−1 |
| Water absorption coefficient at room temperature (ca. 20° C.) | 20 to 300 cm$^{-1}$ |
| Photon source average power (during each pulse) | 0.25 to 10 W |
| Photon output energy | 20 to 1000 mJ per pulse per Tx area |
| Photon source waveform | cw 20 to 2000 ms; 10 to 200 ms between multiple pulses- cw: continuous wave, but instantaneous power can be varied during each "pulse" |
| Treatment geometrical arrangement | Axisymmetric with 2 to 16 treatment (Tx) areas or asymmetric with an even or odd number of Tx areas |
| Treatment shapes | Circular or non-circular, including elliptical, polygonal, arcuate and annular |
| Treatment (Tx) areas | 0.2 to 100 mm$^2$ for each Tx area |
| HAZ stromal depths | 30 to 300 μm for each Tx area |
| Corneal curvature change | 0.1 to 20 D |
| Corneal curvature gradient | 0.1 to 3 D/mm |
| Stromal thermal history - $T_{max}$ depends on heating duration | $T_{max}$ of 50° C. to 100° C. for up to 1 s |
| Heating rate | 5° C./s to 20000° C./s |
| Lower order aberration change | 0.1 to 10 μm for each LOA |
| Higher order aberration change | 0.05 to 1.0 μm for each HOA |
| Aberration change not described by Zernike polynomials up to 8$^{th}$ radial order | 0.05 to 1.0 μm for each aberration |
| Reverse template projections - Shape and location matched to Tx areas | 5 to 200 μm thickness |
| Densification increase within stromal vitrified volumes with external stress | 5% to 200% |
| Adhesion increase between apposed stromal tissue or between donor transplant or synthetic material and host stromal tissue within vitrified volumes | 10% to 1000% |
| Elastic modulus increase within vitrified stromal volumes of at least one of: | |
| Axial modulus (through the cornea from anterior stroma to posterior stroma) | 10% to 1000% |
| Shear modulus | 10% to 1000% |

TABLE 2

Words And/Or Terms Referenced In At Least Some Embodiments Of The Instant Invention.

| Word or Term | Meaning |
| --- | --- |
| Absorption coefficient | Parameter in Beer's law: $I/I_0 = \exp(-\alpha l)$ where $I_0$ and $I$ are the incident and transmitted (to depth l) intensities, respectively, and $\alpha$ is the absorption coefficient (units: cm$^{-1}$ for depth in cm) |
| Densification | Increase in stromal density |
| Elastic modulus | Stress (pressure) required to produce a strain in the material; linear for stromal tissue at low strain (for example, 1% strain) |
| Fast heating | Heating at a rate of 5° C. per second to 20000° C. per second |
| Glass-like | Having some properties characteristic of the non-naturally occurring corneal glass, said properties including but not limited to increased corneal elastic modulus |
| Heat Affected Zone (HAZ) | Volume of material affected by heating |

TABLE 2-continued

Words And/Or Terms Referenced In At Least Some Embodiments Of The Instant Invention.

| Word or Term | Meaning |
| --- | --- |
| Maximum temperature | Maximum temperature $T_{max}$ produced in the HAZ during the thermal history of treatment |
| Moderate temperature | Temperature range (ca. 50 to 100° C.) extending to $T_{max}$ achieved by fast heating of tissue |
| Slow heating | Heating at a rate of 0.001° C. per second to 1° C. per second |
| Thermal damage | Corneal nonstromal cellular necrosis due to heating; noncellular damage processes occur at higher temperature for the same duration of heating compared to cellular necrosis |
| Thermal history | Complete temperature as a function of time |
| Treated volume ($V_{Tx}$) | Tissue within the HAZ treated in the temperature range between the maximum temperature $T_{max}$ to a lower temperature $T_{max}$-5° C. |
| Vitrification | Transformation from a naturally occurring condition to a non-naturally occurring glass-like condition |
| Zernike polynomial | Mathematical term used to describe an optical aberration; some aberrations can be described well by one or a few Zernike polynomials; other aberrations are more complex and are not described predominantly (at least 51%) by Zernike polynomials (and their coefficients) up to and including $8^{th}$ radial order |

What is claimed is:

1. A non-naturally occurring material, produced by vitrifying corneal stromal material using optical energy, wherein the non-naturally occurring vitrified corneal stromal material has the following properties:
    i) a biocompatible glass-like structure,
    ii) an elastic modulus value of 0.33 to 33 MPa,
    iii) a density value of 1.1 to 3.2 g/cm³, and
    iv) a persistent vitrified condition at physiological temperature wherein the persistence is at least one month and the physiological temperature is the range of 30° C to 40° C.

2. The material of claim 1, wherein the non-naturally occurring, vitrified corneal stromal material is configured to be located in a naturally occurring, non-vitrified corneal stromal material wherein a composite material of the vitrified material and the non-vitrified material has the following properties:
    i) the vitrified material of the composite material composes no more than 10% by volume of the composite material; and
    ii) the vitrified material has a spatial volume in which the largest dimension of the vitrified material extends by less than 10 mm into the non-vitrified material.

3. The material of claim 2, wherein the non-naturally occurring, vitrified corneal stromal material is configured to be located in the naturally occurring, non-vitrified corneal material and wherein the such configured to be located non-naturally occurring, vitrified corneal stromal material has at least one of:
    i) a spatial area being between 0.02 and 100 mm² and
    ii) a volume being between 0.001 and 10 mm³.

4. The material of claim 3, wherein the non-naturally occurring, vitrified corneal stromal material comprises spatially separated regions, having a spatial separation within the naturally occurring, non-vitrified corneal material of at least 0.1 mm.

5. The material of claim 3, wherein the non-naturally occurring, vitrified corneal stromal material is located at depths between 0.03 and 0.3 mm relative to an anterior surface of the naturally occurring, non-vitrified corneal stromal material.

6. The material of claim 2, wherein the non-naturally occurring, vitrified corneal stromal material has at least two of the following spatial properties:
    i) a spatial area being between 0.02 and 100 mm²,
    ii) a volume being between 0.001 and 10 mm³,
    iii) a spatial separation within the naturally occurring, non-vitrified corneal material of at least 0.1 mm, and
    iv) being located at depths between 0.03 and 0.3 mm relative to an anterior surface of the non-vitrified corneal stromal material.

7. The material of claim 2, in which at least one of the vitrified corneal stromal material or the non-vitrified corneal stromal material is derived from a corneal stromal tissue.

8. The material of claim 1, wherein the elastic modulus value of the non-naturally occurring, vitrified corneal stromal material is 0.33 to 33 MPa for of at least one of an axial modulus and a shear modulus.

9. The material of claims 8, wherein the material has an elastic modulus value which is 1 to 33 MPa.

10. The material of claim 1, wherein a stromal adhesion value of the non-naturally occurring, vitrified corneal stromal material is 0.08 to 0.8 MPa without a collagen denaturation or melting.

11. The material of claim 1, wherein the material is used for at least one of the following applications:
    i) vision;
    ii) vision improvement;
    iii) a compensation for at least one symptom of: at least one ophthalmic disorder, at least one ophthalmic disease; at least one ophthalmic condition; at least one ophthalmic injury, or any combination thereof;
    iv) a treatment of at least one of: at least one ophthalmic disorder, at least one ophthalmic disease; at least one ophthalmic condition; at least one ophthalmic injury, or any combination thereof;
    v) a stabilization of the treatment; and
    vi) any combination thereof.

12. The material of claim 1, wherein the material has the elastic modulus value which is 1 to 33 MPa.

13. The material of claim 1, wherein the material is produced by localized photothermal heating at a heating rate between 5 degrees per second and 20,000 degrees per second for a heating time required to produce a maximum temperature between 50° C. and 100° C.

* * * * *